(12) United States Patent
Poss et al.

(10) Patent No.: US 6,630,469 B2
(45) Date of Patent: Oct. 7, 2003

(54) 5-HT$_7$ RECEPTOR ANTAGONISTS

(75) Inventors: Michael A. Poss, Lawrenceville, NJ (US); Ashok V. Purandare, Pennington, NJ (US); Ronald J. Mattson, Meriden, CT (US); Li-Qiang Sun, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/841,273

(22) Filed: Apr. 24, 2001

(65) Prior Publication Data

US 2002/0032199 A1 Mar. 14, 2002

Related U.S. Application Data

(60) Provisional application No. 60/202,931, filed on May 9, 2000.

(51) Int. Cl.$^7$ .................. C07D 251/48; C07D 251/54; A61K 31/53; A61P 25/24; A61P 9/17
(52) U.S. Cl. ................ 514/245; 544/197; 544/198; 544/208; 544/209
(58) Field of Search ................ 544/197, 198, 544/208, 209; 514/245

(56) References Cited

U.S. PATENT DOCUMENTS

| | | | |
|---|---|---|---|
| 3,816,629 A | 6/1974 | Irikura et al. | 260/249.6 |
| 3,847,917 A | 11/1974 | Vorbruggen | 260/249.6 |
| 5,491,234 A | 2/1996 | Coe et al. | 544/324 |
| 5,922,122 A | 7/1999 | Takeda et al. | 106/413 |
| 6,117,996 A | 9/2000 | Lowe et al. | 544/216 |
| 6,239,071 B1 * | 5/2001 | Giencke et al. | 544/208 |

FOREIGN PATENT DOCUMENTS

| | | | |
|---|---|---|---|
| DE | 3717480 | | 12/1988 |
| GB | 1288903 | | 11/1972 |
| WO | WO92/18498 | | 10/1992 |
| WO | WO98/15538 | | 4/1998 |
| WO | WO98/34925 | | 8/1998 |
| WO | WO-98 34925 A1 * | | 8/1998 |
| WO | WO99/59499 | | 11/1999 |

OTHER PUBLICATIONS

Clementi et al., European Journal of Pharmacology 393, 3–10, 2000.*

SIPMA, et al., "Regulation of histimine– and UTP–induced increases in Ins(1,4,5)P3, Ins (1,3,4,5)P4 and CA2+ by cyclic AMP in DDT1 MF–2 cells," British Journal of Pharmacology, 1995, 114, 383–390.

Roth, et al. "Binding of Typical and Atypical Antipsychotic Agents to 5–Hydroxytriptamine–6 and 5–Hydroxytryptamine–7 Receptors," Journal of Pharmacology and Experimental Therapeutics, 1994, 268, 3, 1403–1410.

Schwartz, et al., "A Clinician's Primer on the Circadian Clock: Its Localization, Function and Resetting," Advances in Internal Medicine, 193, 38, 81–106.

Leung, et al., "Characterization of putative 5–ht7 receptors mediating direct relaxation in Cynomolgus monkey isolated jugular vein," British Journal of Pharmacology, 1996, 117, 926–930.

Hadjuk, et al., "Novel Inhibitors of Erm Methyltransferases from NMR and Parallel Synthesis," J. Med. Chem., 1999, 42, 3852–3859.

Mohr, et al., "1,2,5–Triazin–2,4–diamine und –2,4,6–triamine mit, H2–antagonistischer Wirkung," Archiv. Der Pharmazie, 319, 86, 878–885.

Chiou, et al., "Effects of Antiglaucoma Drugs on Ocular Blood Flow in Ocular Hypertensive Rabbits," Journal of Ocular Pharmacology, 1993, 9, 1, 13–24.

Eglen, et al., "The 5–HT7 receptor: orphan found," TIPS, 1997, 18, 104–107.

Cushing, et al., "LY215840, a High–Affinity 5–HT7 Receptor Ligand, Blocks Serotonin–Induced Relaxation in Canine Coronary Artery," Journal of Pharmacology and Experimental Therapeutics, 1996, 277, 3, 1560–1566.

Terron, "The 5–HT7 receptor: A target for novel therapeutic avenues?", IDRUGS, 1998, 1, 3, 302–310.

* cited by examiner

*Primary Examiner*—John M. Ford
*Assistant Examiner*—Venkataraman Balasubramanian
(74) *Attorney, Agent, or Firm*—Shah R. Makujina

(57) ABSTRACT

Amino-pyrimidine and amino-triazine derivatives having 5-HT$_7$ antagonist activity for the treatment of sleeping disorders, depression, schizophrenia, anxiety, obsessive compulsive disorders, circadian rhythm disorders, ocular disorders and/or centrally and peripherally mediated hypertension are provided.

18 Claims, No Drawings

5-HT₇ RECEPTOR ANTAGONISTS

CROSS REFERENCE TO RELATED APPLICATION

This non-provisional application claims priority from provisional application U.S. Ser. No. 60/202,931 filed May 9, 2000.

FIELD OF THE INVENTION

The present invention relates to diamino derivatives of pyrimidines and triazines having pharmacological activity at the 5-HT₇ receptor. As such, the compounds are useful for treating various central nervous system and peripheral disorders; as well as disorders of the eye.

BACKGROUND OF THE INVENTION

The 5-HT₇ receptor is a recent member of the growing serotonin receptor family. Both human and animal 5-HT₇ receptors have recently been cloned, expressed and shown to be present in various brain areas and peripheral tissues (Eglen et al., *Trend Pharmacol. Sci.*, 1997, 18, 104–107). The 5-HT₇ receptor has been implicated in the pathophysiology of CNS disorders, such as, sleep disorders, depression, (Schwartz, et al., *Adv. Int. Med.* 1993, 38, 81–106), schizophrenia (Roth, et al., *J. Pharmacol. Exp. Ther.*, 1994, 268, 1403–1410), anxiety, obsessive compulsive disorder, migraine (Terron, *Idrugs*, 1998, 1, 302–310), pain and centrally and peripherally mediated hypertension (Eglen et al., supra).

Although it is not clear which serotonergic receptor(s) activity is responsible for lowering intraocular pressure (IOP), increasing blood flow and providing neuroprotection in the eye, the 5-HT₇ receptor has been found in the retina, choroid and possibly the optic nerve head (May, et al., WO9959499, 4). The stimulation of the 5-HT₇ receptor has caused relaxation of blood vessels in mammals such as the monkey (Leung, et al., *Br. J. Pharmacol.*, 1996, 117, 926–930), dog (Cushing, et al., *J. Pharmacol. Exp. Ther.*, 1996, 277, 1560–1566) and rabbit (Martin, et al., *Br. J. Pharmacol.*, 1995, 114, 383). Stimulation of the 5-HT₇ receptor may therefore improve blood flow to the optic nerve head, macula and the retina, which is believed to be beneficial in the treatment of retinal diseases such as, glaucoma, age related macular degeneration (ARMD), and diabetic retinopathy (Chiou, et al., *J. Ocular Pharmacol.*, 1993, 9, 13–24).

The therapeutic utility of 5-HT₇ receptor ligands for the treatment of CNS and ocular disorders therefore requires the discovery of therapeutic agents with a high affinity for the 5-HT₇ receptor.

SUMMARY OF THE INVENTION

The present invention comprises 5-HT₇ receptor antagonists and partial agonists, useful for the treatment of CNS and ocular disorders. The present invention also comprises methods of treating CNS and ocular disorders in a subject in need thereof comprising the administration of 5-HT₇ antagonists and partial agonists which include compounds described in DE 2163873, DE 3717480, U.S. Pat. No. 5,491,234, WO 92/18498, U.S. Pat. No. 3,816,629, GB 1288903, WO 98/15538, DE 19704922, Mohr et al. Arch. Pharm. (Weinheim, Ger.) 1986, 319(10), 878–885, and Hadjuk et al. in J. Med. Chem. 1999, 42, 3852–3859, incorporated by reference herein.

A first embodiment of a first aspect of the present invention is a method of treating CNS and ocular disorders comprising administration to a subject in need thereof an effective amount of a compound of Formula (I)

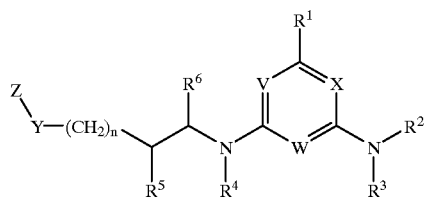

(I)

or a pharmaceutically acceptable salt or hydrate thereof, wherein
V, W and X are CH or N, provided that no more than one of V, W or X can be CH;
Y is O, $S(O)_m$, $CH_2$, $NR^9$ or a covalent bond;
Z is selected from the group consisting of benzodioxolyl, cyclohexenyl, furanyl, indolyl, napthalenyl, thienyl, pyridinyl and phenyl;
  optionally substituted with one to five groups, the same or different independently selected from the group consisting of halogen, $C_{1-4}$alkyl, $C_{1-4}$haloalkyl, O—$C_{1-4}$alkyl, cyano, hydroxy, nitro, $NHSO_2C_{1-6}$alkyl, $NR^7R^8$, $C(O)NH_2$ and $C_{1-3}$alkylene;
m and n are each independently 0, 1 or 2;
$R^1$ is hydrogen, halogen, $C_{1-6}$alkyl, $C_{3-7}$cycloalkyl, or $NR^7R^8$;
  provided that
    if V, W or X is CH, then $R^1$ is not halogen or $NR^7R^8$;
    if V, W and X are each N, then $R^1$ is not hydrogen;
$R^2$ is $C_{1-4}$alkyl substituted with Z', wherein
  Z' is selected from the group consisting of benzodioxolyl, cyclohexenyl, furanyl, indolyl, napthalenyl, thienyl, pyridinyl and phenyl;
  optionally substituted with one to five groups, the same or different independently selected from the group consisting of halogen, $C_{1-4}$alkyl, $C_{1-4}$haloalkyl, O—$C_{1-4}$alkyl, cyano, hydroxy, nitro, $NHSO_2C_{1-6}$alkyl, $NR^7R^8$ and $C(O)NH_2$;
$R^3$ is hydrogen, $C_{1-6}$alkyl or $C_{3-7}$cycloalkyl;
$R^4$ and $R^5$ are independently hydrogen or $C_{1-6}$alkyl or together are $C_{2-3}$alkylene;
$R^6$ is hydrogen or $C_{1-3}$alk(en)ylene
  provided that
    if $R^6$ is $C_{1-3}$alk(en)ylene, it is attached to Z;
$R^7$ and $R^8$ are independently selected from the group consisting of hydrogen, $C_{1-6}$alkyl, $C_{3-7}$cycloalkyl, $SO_2$ $C_{1-6}$alkyl;
  or $R^7$ and $R^8$ together with the nitrogen to which they are attached can form a 5 to 8 membered heterocycle;
  said heterocycle optionally containing a second heteroatom selected from the group consisting of N, O and S;
  said heterocycle being optionally substituted with up to three of the same or different substituents independently selected from $C_{1-6}$alkyl or O—$C_{1-6}$alkyl; and
$R^9$ is hydrogen or $(C_{1-6})$alkyl.

A second embodiment of the first aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) according to the first embodiment of the first aspect.

A first embodiment of a second aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) according the first aspect wherein V and W are each N;
X is CH; and
$R^1$ is H.

A second embodiment of the second aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) according the first aspect wherein V and W are each N;
X is CH;
Z is substituted or unsubstituted phenyl; and
$R^1$ is H.

A third embodiment of the second aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) according to the first aspect wherein V and W are each N;
X is CH;
Y is O or a covalent bond; and
$R^1$ is H.

A fourth embodiment of the second aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) according to the first aspect wherein V and W are each N;
X is CH;
Y is O or a covalent bond;
Z is substituted or unsubstituted phenyl; and
$R^1$ is H.

A fifth embodiment of the second aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) according to the first aspect wherein V and W are each N;
X is CH;
Y is O, S or a covalent bond;
Z is substituted or unsubstituted phenyl, indolyl, pyridinyl, thienyl or benzodioxolyl;
Z' is substituted or unsubstituted phenyl, pyridinyl, indolyl, benzodioxolyl, thienyl. napthenyl or furanyl;
$R^1$ is H;
$R^2$ is $C_{1-3}$alkyl substituted with Z';
$R^{3-6}$ are each H;
m is O; and
n is O or 1.

A sixth embodiment of the second aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) as described in the first aspect of the invention selected from the group consisting of $N^4$-(3,4-Dichlorophenylmethyl)-$N^2$-(2-phenoxyethyl) pyrimidine-2,4-diamine, $N^2$-(2-Phenoxyethyl)-$N^4$-[(1R)-1-phenylpropyl] pyrimidine-2,4-diamine, $N^2$-(2-Phenoxyethyl)-$N^4$-[4-(trifluoromethyl) phenylmethyl]pyrimidine-2,4-diamine, $N^4$-(3,5-Difluorophenylmethyl)-$N^2$-(2-phenoxyethyl) pyrimidine-2,4-diamine, $N^2$-(2-Phenoxyethyl)-$N^4$-[(1R)-1-phenylethyl] pyrimidine-2,4-diamine, $N^4$-[3-Fluoro-5-(trifluoromethyl)phenylmethyl]-$N^2$-(2-phenoxyethyl)pyrimidine-2,4-diamine, $N^4$-(3,5-Dimethoxyphenylmethyl)-$N^2$-(2-phenoxyethyl) pyrimidine-2,4-diamine, $N^4$-(1-Phenylethyl)-$N^2$-[2-(3-pyridinyl)ethyl]pyrimidine-2,4-diamine, Compound 1, $N^4$-(3,4-Dichlorophenylmethyl)-$N^2$-(2-phenylethyl) pyrimidine-2,4-diamine, $N^4$-(2-Furanylmethyl)-$N^2$-(2-phenylethyl)pyrimidine-2,4-diamine, Compound 2

$N^4$-(3-Chloro-4-methylphenylmethyl)-$N^2$-(2-phenylethyl)pyrimidine-2,4-diamine, $N^2$-[2-(4-Methoxyphenyl)ethyl]-$N^4$-(1-phenylethyl) pyrimidine-2,4-diamine, $N^4$-(3-Chlorophenylmethyl)-$N^2$-(2-phenylethyl) pyrimidine-2,4-diamine, $N^2$-(2-Phenylethyl)-$N^4$-[(1R)-1-phenylethyl]pyrimidine-2,4-diamine, $N^2$-(2-Phenylethyl)-$N^4$-[4-(trifluoromethyl) phenylmethyl]pyrimidine-2,4-diamine, $N^4$-[4-Fluoro-3-(trifluoromethyl)phenylmethyl]-$N^2$-(2-phenylethyl)pyrimidine-2,4-diamine, $N^2$-[2-(4-Benzodioxolyl)ethyl]-$N^4$-(1-phenylethyl) pyrimidine-2,4-diamine and $N^2$-[2-(5-Fluoro-1H-indol-3-yl)ethyl]-$N^4$-(1-phenylethyl)pyrimidine-2,4-diamine, Compound 3, $N^4$-(2-Furanylmethyl)-$N^2$-(2-phenoxyethyl)pyrimidine-2,4-diamine, Compound 4, and $N^2$-(2-Phenylethyl)-$N^4$-(4-pyridinylmethyl)pyrimidine-2,4-diamine, Compound 5.

A seventh embodiment of the second aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) as described in the first aspect of the invention selected from the group consisting of $N^4$-(3-Fluorophenylmethyl)-$N^2$-(2-phenoxyethyl) pyrimidine-2,4-diamine, $N^4$-[4-Fluoro-3-(trifluoromethyl)phenylmethyl]-$N^2$-(2-phenoxyethyl)pyrimidine-2,4-diamine, $N^4$-[3-(Aminocarbonyl)phenylmethyl]-$N^2$-(2-phenoxyethyl)pyrimidine-2,4-diamine, Compound 6, $N^4$-[(1R)-1-(4-Methylphenyl)ethyl]-$N^2$-(2-phenoxyethyl) pyrimidine-2,4-diamine, $N^4$-(1-Phenylethyl)-$N^2$-(2-phenylpropyl)pyrimidine-2,4-diamine, $N^4$-(1-Phenylethyl)-$N^2$-(3-phenylpropyl)pyrimidine-2,4-diamine, $N^2$-(2-Phenthioethyl)-$N^4$-(1-phenylethyl)pyrimidine-2,4-diamine, $N^2$-[2-(4-Chlorophenyl)ethyl]-$N^4$-(1-phenylethyl) pyrimidine-2,4-diamine, $N^4$-[2-(1H-Indol-3-yl)ethyl]-$N^2$-(1-phenylethyl) pyrimidine-2,4-diamine, Compound 7, $N^2$-(2-Phenylethyl)-$N^4$-[(1R)-1-phenylpropyl] pyrimidine-2,4-diamine, $N^2$-[2-(3-Bromophenyl)ethyl]-$N^4$-(1-phenylethyl) pyrimidine-2,4-diamine, Compound 8, $N^2$-[2-(4-Bromophenyl)ethyl]-$N^4$-(1-phenylethyl) pyrimidine-2,4-diamine, Compound 9, $N^4$-(2,4-Dichlorophenylmethyl)-$N^2$-(2-phenylethyl) pyrimidine-2,4-diamine, $N^2$-[2-(3,4-Dichlorophenyl)ethyl]-$N^4$-(1-phenylethyl) pyrimidine-2,4-diamine, $N^2$-(lndan-2-yl)-N4-(1-phenylethyl)pyrimidine-2,4-diamine, Compound 10, $N^2$-(2-Phenylethyl)-$N^4$-(3-pyridinylmethyl)pyrimidine-2,4-diamine, Compound 11, $N^4$-(1-Phenylethyl)-$N^2$-{2-[3-(trifluoromethyl)phenyl] ethyl}pyrimidine-2,4-diamine, $N^2$-[2-(2-Methoxyphenyl)ethyl]-$N^4$-(1-phenylethyl) pyrimidine-2,4-diamine, and $N^4$-(1-Phenylethyl)-$N^2$-[2-(2-pyridinyl)ethyl]pyrimidine-2,4-diamine, Compound 12.

An eighth embodiment of the second aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) as described in the first aspect of the invention selected from the group consisting of $N^4$-[(1S)-1-(4-Bromophenyl)ethyl]-$N^2$-(2-phenoxyethyl) pyrimidine-2,4-diamine, Compound 13, $N^4$-(3-Methylphenylmethyl)-$N^2$-(2-phenoxyethyl) pyrimidine-2,4-diamine, $N^2$-(2-Phenoxyethyl)-$N^4$-[(1S)-1-phenylethyl]pyrimidine-2,4-diamine, $N^4$-{3-[(Methylsulfonyl)amino]phenylmethyl}-$N^2$-(2-phenoxyethyl)pyrimidine-2,4-diamine, Compound 14, $N^2$-(2-Phenoxyethyl)-$N^4$-[3-(trifluoromethyl) phenylmethyl]pyrimidine-2,4-diamine, $N^4$-(3-Chlorophenylmethyl)-$N^2$-(2-phenoxyethyl) pyrimidine-2,4-diamine, $N^2$-(2-Phenoxyethyl)-$N^4$-[(1S)-1-phenylpropyl] pyrimidine-2,4-diamine, $N^4$-(4-Chlorophenylmethyl)-$N^2$-(2-phenoxyethyl) pyrimidine-2,4-diamine, $N^4$-(3-Iodophenylmethyl)-$N^2$-(2-phenoxyethyl) pyrimidine-2,4-diamine, Compound 15, $N^4$-(3,4-Difluorophenylmethyl)-$N^2$-(2-phenoxyethyl) pyrimidine-2,4-diamine, $N^4$-(4-Benzodioxolylmethyl)-$N^2$-(2-phenoxyethyl) pyrimidine-2,4-diamine, $N^2$-(2-Phenoxyethyl)-$N^4$-(phenylmethyl)pyrimidine-2,4-diamine, $N^4$-(3-Methylphenylmethyl)-$N^2$-(2-phenoxyethyl) pyrimidine-2,4-diamine, $N^4$-(3-Chloro-4-methylphenylmethyl)-$N^2$-(2-phenoxyethyl)pyrimidine-2,4-diamine, $N^4$-[1-(4-Chlorophenyl)ethyl]-$N^2$-(2-phenoxyethyl) pyrimidine-2,4-diamine, $N^4$-(1-Napthalenylmethyl)-$N^2$-(2-phenoxyethyl) pyrimidine-2,4-diamine, Compound 16, $N^4$-[(1S)-1-(1-Napthalenyl)ethyl]-$N^2$-(2-phenoxyethyl) pyrimidine-2,4-diamine, Compound 17, $N^2$-(2-Phenoxyethyl)-$N^4$-(2-thienylmethyl)pyrimidine-2,4-diamine, Compound 18, $N^4$-[(1S)-1-(4-Methylphenyl)ethyl]-$N^2$-(2-phenoxyethyl) pyrimidine-2,4-diamine, $N^4$-[4-(1-Methylethyl)phenylmethyl]-$N^2$-(2-phenoxyethyl)pyrimidine-2,4-diamine, $N^4$-[2-Fluoro-5-(trifluoromethyl)phenylmethyl]-$N^2$-(2-phenoxyethyl)pyrimidine-2,4-diamine, $N^2$-(2-Phenoxyethyl)-$N^4$-(4-pyridinylmethyl)pyrimidine-2,4-diamine, Compound 19, $N^4$-(3-Chloro-4-fluorophenylmethyl)-$N^2$-(2-phenoxyethyl)pyrimidine-2,4-diamine, $N^2$-(2-Phenoxyethyl)-$N^4$-(3-pyridinylmethyl)pyrimidine-2,4-diamine, Compound 20, $N^2$-[2-(3-Hydroxyphenyl)ethyl]-$N^4$-(1-phenylethyl) pyrimidine-2,4-diamine, Compound 21, $N^4$-[(1S)-1-Phenylethyl]-$N^2$-(2-phenylethyl)pyrimidine-2,4-diamine, $N^2$-(2-Phenylethyl)-$N^4$-[(1S)-1-phenylpropyl] pyrimidine-2,4-diamine, $N^2$-[2-(4-Hydroxyphenyl)ethyl]-$N^4$-(1-phenylethyl) pyrimidine-2,4-diamine, $N^2$-[2-(3-Fluorophenyl)ethyl]-$N^4$-(1-phenylethyl) pyrimidine-2,4-diamine, $N^4$-[1-(4-Fluorophenyl)ethyl]-$N^2$-(2-phenoxyethyl) pyrimidine-2,4-diamine, $N^2$-[2-(2-Fluorophenyl)ethyl]-$N^4$-(1-phenylethyl) pyrimidine-2,4-diamine, $N^4$-(2-Methoxyphenylmethyl)-$N^2$-(2-phenoxyethyl) pyrimidine-2,4-diamine, $N^2$-[2-(3-Methoxyphenyl)ethyl]-$N^4$-(1-phenylethyl) pyrimidine-2,4-diamine, $N^2$-[2-(3-Fluorophenyl)ethyl]-$N^4$-(1-phenylethyl) pyrimidine-2,4-diamine, $N^2$-[2-(4-Fluorophenyl)ethyl]-$N^4$-(1-phenylethyl) pyrimidine-2,4-diamine, $N^2$-[2-(3-Cyanophenyl)ethyl]-$N^4$-(1-phenylethyl) pyrimidine-2,4-diamine, Compound 22, $N^2$-[2-(1-Cyclohexenyl)ethyl]-$N^4$-(1-phenylethyl) pyrimidine-2,4-diamine, Compound 23, $N^2$-[2-(3-Chlorophenyl)ethyl]-$N^4$-(1-phenylethyl) pyrimidine-2,4-diamine, $N^4$-[(1S)-1-(1-Napthalenyl)ethyl]-$N^2$-(2-phenylethyl) pyrimidine-2,4-diamine, Compound 24, $N^4$-(1-Methyl-1-phenyl)ethyl)-$N^2$-(2-phenylethyl) pyrimidine-2,4-diamine, $N^4$-(3-Iodophenylmethyl)-$N^2$-(2-phenylethyl)pyrimidine-2,4-diamine, Compound 25, $N^2$-(2-Phenylethyl)-$N^4$-(phenylmethyl)pyrimidine-2,4-diamine, $N^4$-(3-Methylphenylmethyl)-$N^2$-(2-phenylethyl) pyrimidine-2,4-diamine, $N^4$-(4-Chlorophenylmethyl)-$N^2$-(2-phenylethyl) pyrimidine-2,4-diamine, $N^4$-(3-Bromophenylmethyl)-$N^2$-(2-phenylethyl) pyrimidine-2,4-diamine, Compound 26, $N^4$-(3-Fluorophenylmethyl)-$N^2$-(2-phenylethyl) pyrimidine-2,4-diamine, $N^2$-(2-Phenylethyl)-$N^4$-(2-thienylmethyl)pyrimidine-2,4-diamine, Compound 27, $N^4$-[1-(4-Chlorophenyl)ethyl]-$N^2$-(2-phenylethyl) pyrimidine-2,4-diamine, $N^2$-[2-(4-Methylphenyl)ethyl]-$N^4$-(1-phenylethyl) pyrimidine-2,4-diamine, $N^2$-(Methyl)-$N^2$-(2-phenylethyl)-$N^4$-(1-phenylethyl) pyrimidine-2,4-diamine, $N^4$-(3,4-Difluorophenylmethyl)-$N^2$-(2-phenylethyl) pyrimidine-2,4-diamine, $N^4$-(4-Benzodioxolylmethyl)-$N^2$-(2-phenylethyl) pyrimidine-2,4-diamine, $N^4$-(2-Chlorophenylmethyl)-$N^2$-(2-phenylethyl) pyrimidine-2,4-diamine, $N^4$-(3-Chloro-4-fluorophenylmethyl)-$N^2$-(2-phenylethyl) pyrimidine-2,4-diamine, $N^4$-(3-Methoxyphenylmethyl)-$N^2$-(2-phenylethyl) pyrimidine-2,4-diamine, $N^4$-(4-Methoxyphenylmethyl)-$N^2$-(2-phenylethyl) pyrimidine-2,4-diamine, $N^2$-(2-Phenylethyl)-$N^4$-[3-(trifluoromethyl) phenylmethyl]pyrimidine-2,4-diamine, $N^2$-[2-(1H-Indol-1-yl)ethyl]-$N^4$-(1-phenylethyl) pyrimidine-2,4-diamine, Compound 28, $N^4$-(1-Phenylethyl)-$N^2$-[2-(2-thienyl)ethyl]pyrimidine-2,4-diamine, Compound 29, $N^2$-[2(1H-Indol-3-yl)ethyl]-$N^2$-(methyl)-$N^4$-(1-phenylethyl)pyrimidine-2,4-diamine, Compound 30 and $N^2$-[2-(6-Fluoro-1H-indol-3-yl)ethyl]-$N^4$-(1-phenylethyl) pyrimidine-2,4-diamine, Compound 31.

A ninth embodiment of the second aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) according the first aspect wherein V and W are each N;

X is CH; and $R^1$ is $C_{1-6}$alkyl or $C_{3-7}$cycloalkyl.

An tenth embodiment of the second aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) as described in the first aspect of the invention selected from the group consisting of $N^2$-[2-(3-Fluorophenyl)ethyl]-6-methyl-$N^4$-[(1S)-1-phenylethyl]pyrimidine-2,4-diamine, $N^2$-[2-(3-Methoxyphenyl)ethyl]-6-methyl-$N^4$-[(1S)-1-phenylethyl]pyrimidine-2,4-diamine, $N^2$-[2-(3-Bromophenyl)ethyl]-6-methyl-$N^4$-[(1S)-1-phenylethyl]pyrimidine-2,4-diamine, $N^2$-[2-(3-Cyanophenyl)ethyl]-6-methyl-$N^4$-[(1S)-1-phenylethyl]pyrimidine-2,4-diamine, $N^2$-[2-(4-Chlorophenyl)ethyl]-6-methyl-$N^4$-[(1S)-1-phenylethyl]pyrimidine-2,4-diamine, $N^2$-[2-(4-Methylphenyl)ethyl]-6-methyl-$N^4$-[(1S)-1-phenylethyl]pyrimidine-2,4-diamine, $N^2$-[2-(2-Methoxyphenyl)ethyl]-6-methyl-$N^4$-[(1S)-1-phenylethyl]pyrimidine-2,4-diamine, $N^2$-[2-(3,5-Dimethoxyphenyl)ethyl]-6-methyl-$N^4$-[(1S)-1-phenylethyl]pyrimidine-2,4-diamine, $N^2$-[2-(3-Bromo-4-methoxyphenyl)ethyl]-6-methyl-$N^4$-[(1S)-1-phenylethyl]pyrimidine-2,4-diamine, $N^2$-[2-(4-Methoxyphenyl)ethyl]-6-methyl-$N^4$-[(1S)-1-phenylethyl]pyrimidine-2,4-diamine, and $N^2$-[2-(3-Acetamidophenyl)ethyl]-6-methyl-$N^4$-[(1S)-1-phenylethyl]pyrimidine-2,4-diamine.

A first embodiment of a third aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) according to the first aspect wherein X and W are each N;

V is CH; and $R^1$ is H.

An second embodiment of the third aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) as described in the first aspect of the invention said compound being $N^4$-[2-(4-Fluorophenoxy)ethyl]-$N^2$-(1-phenylethyl)pyrimidine-2,4-diamine.

A first embodiment of a fourth aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) according to the first aspect wherein X and V are each N;

W is CH; and $R^1$ is H.

A second embodiment of the fourth aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) as described in the first aspect of the invention selected from the group consisting of $N^4$-[2-(4-Aminophenyl)ethyl]-$N^6$-[(1S)-1-phenylethyl] pyrimidine-4,6-diamine, and $N^4$-[2-(4-Bromoophenyl)ethyl]-$N^6$-[(1S)-1-phenylethyl] pyrimidine-4,6-diamine.

A third embodiment of the fourth aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) as described in the first aspect of the invention selected from the group consisting of $N^4$-[2-(4-Hydroxyphenyl)ethyl]-$N^6$-[(1S)-1-phenylethyl] pyrimidine-4,6-diamine, and $N^4$-[2-(4-Fluorophenoxy)ethyl]-$N^6$-[(1S)-1-phenylethyl] pyrimidine-4,6-diamine, Example 16.

A first embodiment of a fifth aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) according to the first embodiment of the first aspect wherein V, W and X are each N; and $R^1$ is $NH_2$.

A second embodiment of a fifth aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) according to the first embodiment of the first aspect wherein V, W and X are each N;

$R^1$ is $NH_2$; and

Y is O.

A second embodiment of the fifth aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) as described in the first aspect of the invention selected from the group consisting of $N^2$-[2-(4-Chlorophenyl)ethyl]-$N^4$-[(1S)-1-phenylpropyl]-1,3,5-triazine-2,4,6-triamine, Compound 32, $N^2$-[2-(3,4-Dichlorophenyl)ethyl]-$N^4$-[(1S)-1-phenylpropyl]-1,3,5-triazine-2,4,6-triamine, Compound 33, $N^2$-[(1S)-1-(4-Bromophenyl)ethyl]-$N^4$-[2-(4-methylphenyl)ethyl]-1,3,5-triazine-2,4,6-triamine, Compound 34, $N^2$-[(1S)-1-Phenylpropyl]-$N^4$-(2-phenylpropyl)-1,3,5-triazine-2,4,6-triamine, Compound 35, $N^2$-[(1S)-1-Phenylpropyl]-$N^4$-[2-(3-(trifluoromethyl)phenyl)ethyl]-1,3,5-triazine-2,4,6-triamine, Compound 36, $N^2$-[(1S)-1-Phenylethyl]-$N^4$-(2-phenylpropyl)-1,3,5-triazine-2,4,6-triamine, Compound 37, $N^2$-[(1S)-1-(1-Napthalenyl)ethyl]-$N^4$-[2-(phenylamino)ethyl]-1,3,5-triazine-2,4,6-triamine, Compound 38, and $N^2$-[2-(4-Bromophenyl)ethyl]-$N^4$-[(1S)-1-(4-nitrophenyl)ethyl]-1,3,5-triazine-2,4,6-triamine, Compound 39.

A third embodiment of the fifth aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) as described in the first aspect of the invention selected from the group consisting of $N^2$-[2-(Phenoxy)ethyl]-$N^4$-[(1S)-1-phenylpropyl]-1,3,5-triazine-2,4,6-triamine, Compound 40, $N^2$-[2-(Phenoxy)ethyl]-$N^4$-[(1S)-1-phenylethyl]-1,3,5-triazine-2,4,6-triamine, Compound 41, Example 19–20, $N^2$-[(1S)-1-(1-Napthyl)ethyl]-$N^4$-[2-(phenoxy)ethyl]-1,3,5-triazine-2,4,6-triamine, Compound 42, $N^2$-[2-(4-Fluorophenoxy)ethyl]-$N^4$-[1-(4-fluorophenyl)ethyl]-1,3,5-triazine-2,4,6-triamine, Compound 43, $N^2$-[2-(4-Fluorophenoxy)ethyl]-$N^4$-[(1S)-1-(4-fluorophenyl)ethyl]-1,3,5-triazine-2,4,6-triamine, Compound 44, $N^2$-[2-(4-Fluorophenoxy)ethyl]-$N^4$-[(1S)-1-(4-nitrophenyl)ethyl]-1,3,5-triazine-2,4,6-triamine, Compound 45, $N^2$-[2-(4-Fluorophenoxy)ethyl]-$N^4$-[(1R)-1-(4-fluorophenyl)ethyl]-1,3,5-triazine-2,4,6-triamine, Compound 46, $N^2$-[2-(3,4-Difluorophenoxy)ethyl]-$N^4$-[(1S)-1-(4-nitrophenyl)ethyl]-1,3,5-triazine-2,4,6-triamine, Compound 47, $N^2$-[2-(2-Fluorophenyl)ethyl]-$N^4$-[(1S)-1-phenylethyl]-1,3,5-triazine-2,4,6-triamine, Compound 48, $N^2$-[2-(4-Methylphenyl)ethyl]-$N^4$-[(1S)-1-phenylpropyl]-1,3,5-triazine-2,4,6-triamine, Compound 49, $N^2$-[2-(4-Chlorophenyl)ethyl]-$N^4$-[(1S)-1-phenylethyl]-1,3,5-triazine-2,4,6-triamine, Compound 50, $N^2$-[2-(2-Fluorophenyl)ethyl]-$N^4$-[(1S)-1-phenylpropyl]-1,3,5-triazine-2,4,6-triamine, Compound 51, $N^2$-[2-(3-Methoxyphenyl)ethyl]-$N^4$-[(1S)-1-phenylpropyl]-1,3,5-triazine-2,4,6-triamine, Compound 52, $N^2$-[(1S)-1-Phenylethyl]-$N^4$-{2-[3-(trifluoromethyl)phenyl]ethyl}-1,3,5-triazine-2,4,6-triamine, Compound 53, $N^2$-[2-(3-Methoxyphenyl)ethyl]-$N^4$-[(1S)-1-phenylethyl]-1,3,5-triazine-2,4,6-triamine, Compound 54, $N^2$-[2-(3-Cyanophenyl)ethyl]-$N^4$-[(1S)-1-phenylethyl]-1,3,5-triazine-2,4,6-triamine, Compound 55, $N^2$-[(1S)-1-(1-Napthalenyl)ethyl]-$N^4$-(2-phenylethyl)-1,3,5-triazine-2,4,6-triamine, Compound 56, $N^2$-[2-(1-Cyclohexenyl)ethyl]-$N^4$-[(1S)-1-phenylethyl]-1,3,5-triazine-2,4,6-triamine, Compound 57

$N^2$-[2-(3-Chlorophenyl)ethyl]-$N^4$-[(1S)-1-(4-nitrophenyl)ethyl]-1,3,5-triazine-2,4,6-triamine, Compound 58 and $N^2$-[2-(4-Chlorophenyl)ethyl]-$N^4$-[(1S)-1-(4-nitrophenyl)ethyl]-1,3,5-triazine-2,4,6-triamine, Compound 59.

A fourth embodiment of the fifth aspect of the present invention is a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (I) as described in the first aspect of the invention selected from the group consisting of N²-[(1S)-1-Phenylethyl]-N⁴-(2-phenylethyl)-1,3,5-triazine-2,4,6-triamine, Compound 60, N²-[2-(3-Fluorophenyl)ethyl]-N⁴-[(1S)-1-phenylethyl]-1,3,5-triazine-2,4,6-triamine, Compound 61, N²-[2-(3-Chlorophenyl)ethyl]-N⁴-[(1S)-1-phenylethyl]-1,3,5-triazine-2,4,6-triamine, Compound 62, N²-[2-(3-Fluorophenyl)ethyl]-N⁴-[(1S)-1-phenylpropyl]-1,3,5-triazine-2,4,6-triamine, Compound 63, N²-[2-(4-Fluorophenyl)ethyl]-N⁴-[(1S)-1-phenylethyl]-1,3,5-triazine-2,4,6-triamine, Compound 64, N²-2-Phenylethyl-N⁴-[(1S)-1-phenylpropyl]-1,3,5-triazine-2,4,6-triamine, Compound 65, N²-[2-(3-Bromophenyl)ethyl]-N⁴-[(1S)-1-phenylethyl]-1,3,5-triazine-2,4,6-triamine, Compound 66, N²-[2-(4-Fluorophenyl)ethyl]-N⁴-[(1S)-1-phenylpropyl]-1,3,5-triazine-2,4,6-triamine, Compound 67, N²-[(1S)-1-(4-Bromophenyl)ethyl]-N⁴-[2-(3-fluorophenyl)ethyl]-1,3,5-triazine-2,4,6-triamine, Compound 68, N²-[2-(3-Chlorophenyl)ethyl]-N⁴-[(1S)-1-phenylpropyl]-1,3,5-triazine-2,4,6-triamine, Compound 69, N²-[(1S)-1-(4-Bromophenyl)ethyl]-N⁴-[2-(4-fluorophenyl)ethyl]-1,3,5-triazine-2,4,6-triamine, Compound 70, N²-[2-(3,4-Dichlorophenyl)ethyl]-N⁴-[(1S)-1-phenylethyl]-1,3,5-triazine-2,4,6-triamine, Compound 71, N²-[2-(4-Methylphenyl)ethyl]-N⁴-[(1S)-1-phenylethyl]-1,3,5-triazine-2,4,6-triamine, Compound 72, N²-[2-(3-Hydroxyphenyl)ethyl]-N⁴-[(1S)-1-phenylethyl]-1,3,5-triazine-2,4,6-triamine, Compound 73, N²-[2-(4-Fluorophenyl)ethyl]-N⁴-[(1S)-1-(4-nitrophenyl)ethyl]--1,3,5-triazine-2,4,6-triamine, Compound 74, N²-[2-(4-Hydroxyphenyl)ethyl]-N⁴-[(1S)-1-(4-nitrophenyl)ethyl]-1,3,5-triazine-2,4,6-triamine, Compound 75, N²-[2-(2-Fluorophenyl)ethyl]-N⁴-[(1S)-1-(4-nitrophenyl)ethyl]-1,3,5-triazine-2,4,6-triamine, Compound 76, N²-[2-(3-Methoxyphenyl)ethyl]-N⁴-[(1S)-1-(4-nitrophenyl)ethyl]-1,3,5-triazine-2,4,6-triamine, Compound 77, N²-[2-(4-Aminophenyl)ethyl]-N⁴-[(1S)-1-(4-nitrophenyl)ethyl]-1,3,5-triazine-2,4,6-triamine, Compound 78, N²-[2-(4-Methylphenyl)ethyl]-N⁴-[(1S)-1-(4-nitrophenyl)ethyl]-1,3,5-triazine-2,4,6-triamine, Compound 79, N²-[2-(4-Hydroxy-3-methoxyphenyl)ethyl]-N⁴-[(1S)-1-(4-nitrophenyl)ethyl]-1,3,5-triazine-2,4,6-triamine, Compound 80, N²-[(1S)-1-(4-Fluorophenyl)ethyl]-N⁴-[2-(4-fluorophenyl)ethyl]-1,3,5-triazine-2,4,6-triamine, Example 17, N²-[(1S)-1-(4-Fluorophenyl)ethyl]-N⁴-[2-(2-pyridinyl)ethyl]-1,3,5-triazine-2,4,6-triamine, Example 18, 21, and N²-(2-Chlorophenylmethyl)-N⁴-(2-phenylethyl)-1,3,5-triazine-2,4,6-triamine.

A first embodiment of a sixth aspect of the present invention are compounds of Formula (I)

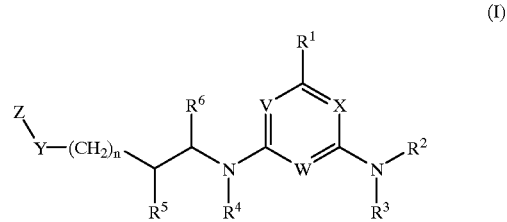

(I)

or a pharmaceutically acceptable salts or hydrates thereof, wherein

V, W and X are each N, or V and X are each N and W is CH;

Y is O, S(O)$_m$, CH$_2$, NR$^9$ or a covalent bond;

Z is selected from the group consisting of benzodioxolyl, cyclohexenyl, furanyl, indolyl, napthalenyl, thienyl, pyridinyl and phenyl;

optionally substituted with one to five groups, the same or different independently selected from the group consisting of halogen, C$_{1-4}$alkyl, C$_{1-4}$haloalkyl, O—C$_{1-4}$alkyl, cyano, hydroxy, nitro, NH SO$_2$ C$_{1-6}$alkyl, NR$^7$R$^8$, C(O)NH$_2$ and C$_{1-3}$alkylene;

m and n are each independently 0, 1 or 2;

R$^1$ is hydrogen, halogen or NR$^7$R$^8$;

provided that if W is CH, then R$^1$ is not halogen or NR$^7$R$^8$;

if V, W and X are each N, then R$^1$ is not hydrogen;

R$^2$ is C$_{1-4}$alkyl substituted with Z', wherein

Z' is selected from the group consisting of benzodioxolyl, cyclohexenyl, furanyl, indolyl, napthalenyl, thienyl, pyridinyl and phenyl;

optionally substituted with one to five groups, the same or different independently selected from the group consisting of halogen, C$_{1-4}$alkyl, C$_{1-4}$haloalkyl, O—C$_{1-4}$alkyl, cyano, hydroxy, nitro, NH SO$_2$ C$_{1-6}$alkyl, NR$^7$R$^8$ and C(O)NH$_2$;

R$^3$ is hydrogen, C$_{1-6}$alkyl or C$_{3-7}$cycloalkyl;

R$^4$ and R$^5$ are independently hydrogen or C$_{1-6}$alkyl or together are C$_{2-3}$alkylene;

R$^6$ is hydrogen or C$_{1-3}$alk(en)ylene provided that if R$^6$ is C$_{1-3}$alk(en)ylene, it is attached to Z;

R$^7$ and R$^8$ are independently selected from the group consisting of hydrogen, C$_{1-6}$alkyl, C$_{3-7}$cycloalkyl, SO$_2$ C$_{1-6}$alkyl;

or R$^7$ and R$^8$ together with the nitrogen to which they are attached form a 5 to 8 membered heterocycle;

said heterocycle optionally containing a second heteroatom selected from the group consisting of N, O and S;

said heterocycle being optionally substituted with up to three of the same or different substituents independently selected from C$_{1-6}$alkyl or O—C$_{1-6}$alkyl; and R$^9$ is hydrogen or (C$_{1-6}$)alkyl.

A second embodiment of the sixth aspect of the present invention are compounds of formula (I) according to the first embodiment of the sixth aspect, wherein V, W and X are each N.

A third embodiment of the sixth aspect of the present invention are compounds of formula (I) according to the first embodiment of the sixth aspect, wherein V and X are each N and W is CH.

A fourth embodiment of the sixth aspect of the present invention are compounds of formula (I) according to the first embodiment of the sixth aspect, wherein Y is $NR^9$.

A fifth embodiment of the sixth aspect of the present invention are compounds of formula (I) according to the first embodiment of the sixth aspect, wherein Z is selected from the group consisting of benzodioxolyl, cyclohexenyl, furanyl, indolyl, napthalenyl, thienyl and pyridinyl;
optionally substituted with one to five groups, the same or different independently selected from the group consisting of halogen, $C_{1-4}$alkyl, $C_{1-4}$haloalkyl, O—$C_{1-4}$alkyl, cyano, hydroxy, nitro, NH $SO_2$ $C_{1-6}$alkyl, $NR^7R^8$, $C(O)NH_2$ and $C_{1-3}$alkylene; and Z' is selected from the group consisting of benzodioxolyl, cyclohexenyl, furanyl, indolyl, napthalenyl, thienyl and pyridinyl;
optionally substituted with one to five groups, the same or different independently selected from the group consisting of halogen, $C_{1-4}$alkyl, $C_{1-4}$haloalkyl, O—$C_{1-4}$alkyl, cyano, hydroxy, nitro, NH $SO_2$ $C_{1-6}$alkyl, $NR^7R^8$ and $C(O)NH_2$.

A sixth embodiment of the sixth aspect of the present invention are compounds of formula (1) according to the first embodiment of the sixth aspect, wherein Z' is selected from the group consisting of benzodioxolyl, cyclohexenyl, furanyl, indolyl, napthalenyl, thienyl and pyridinyl;
optionally substituted with one to five groups, the same or different independently selected from the group consisting of halogen, $C_{1-4}$alkyl, $C_{1-4}$haloalkyl, O—$C_{1-4}$alkyl, cyano, hydroxy, nitro, NH $SO_2$ $C_{1-6}$alkyl, $NR^7R^8$ and $C(O)NH_2$.

A seventh embodiment of the sixth aspect of the present invention are compounds of formula (I) according to the first embodiment of the sixth aspect, wherein Z is selected from the group consisting of benzodioxolyl, cyclohexenyl, furanyl, indolyl, napthalenyl, thienyl and pyridinyl;
optionally substituted with one to five groups, the same or different independently selected from the group consisting of halogen, $C_{1-4}$alkyl, $C_{1-4}$haloalkyl, O—$C_{1-4}$alkyl, cyano, hydroxy, nitro, NH $SO_2$ $C_{1-6}$alkyl, $NR^7R^8$, $C(O)NH_2$ and $C_{1-3}$alkylene.

A first embodiment of a seventh aspect of the present invention are compounds of formula (Ia)

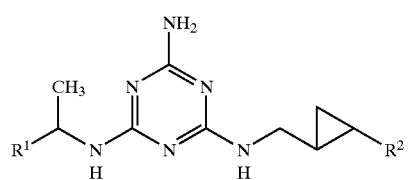

(Ia)

and pharmaceutically acceptable salts and solvates thereof, wherein $R^1$ is phenyl optionally substituted with one or more of the same or different halogens; and $R^2$ is phenyl or pyridyl optionally substituted with one or more of the same or different halogens.

A second embodiment of the seventh aspect of the present invention are compounds according to the first embodiment of the seventh aspect of the present invention wherein $R^1$ is phenyl optionally substituted with one or more of the same halogens; and $R^2$ is phenyl or pyridyl optionally substituted with one or more of the same halogens.

A third embodiment of the seventh aspect of the present invention are compounds according to the first embodiment of the seventh aspect of the present invention wherein $R^1$ is phenyl optionally substituted with one halogen; and $R^2$ is phenyl or pyridyl optionally substituted with one halogen.

A fourth embodiment of the seventh aspect of the present invention are compounds according to the first embodiment of the seventh aspect of the present invention wherein $R^1$ is phenyl optionally substituted with fluoro; and $R^2$ is phenyl or pyridyl optionally substituted with fluoro.

A fifth embodiment of the seventh aspect of the present invention are compounds according to the first embodiment of the seventh aspect of the present invention wherein $R^1$ is unsubstituted phenyl; and $R^2$ is monofluoro-phenyl or unsubstituted pyridyl.

A sixth embodiment of the seventh aspect of the present invention are compounds according to the first embodiment of the seventh aspect of the present invention wherein $R^2$ is unsubstituted 4-pyridyl.

A seventh embodiment of the seventh aspect of the present invention are compounds according to the first embodiment of the seventh aspect of the present invention selected from the group consisting of (S,S)-trans-N-[2-(4-Fluoro-phenyl)-cyclopropylmethyl]-N'-(1-phenyl-ethyl)-[1,3,5]triazine-2,4,6-triamine, (S,S)-trans-N-[2-(2-Fluoro-phenyl)-cyclopropylmethyl]-N'-(1-phenyl-ethyl)-[1,3,5]triazine-2,4,6-triamine, (±)-trans-N-(1-Phenyl-ethyl)-N'-(2-pyridin-4-yl-cyclopropylmethyl)-[1,3,5]triazine-2,4,6-triamine, (±)-trans-N-[2-(2-Fluoro-phenyl)-cyclopropylmethyl]-N'-(1-phenyl-ethyl)-[1,3,5]triazine-2,4,6-triamine, (S,S)-trans-N-[2-(4-Fluoro-phenyl)-cyclopropylmethyl]-N'-[1-(4-fluoro)phenyl-ethyl]-[1,3,5]triazine-2,4,6-triamine and (±)-trans-N-[2-(4-Fluoro-phenyl)-cyclopropylmethyl]-N'-(1-phenyl-ethyl)-[1,3,5]triazine-2,4,6-triamine.

Embodiments of an eighth aspect of the present invention comprise a method of treating CNS and ocular disorders comprising administration to a subject in need thereof an effective amount of a compound of Formula (Ia) as described in the seventh aspect of the present invention.

Embodiments of a ninth aspect of the present invention comprise a method of treating sleeping disorders, depression, schizophrenia, anxiety, obsessive compulsive disorders, circadian rhythm disorders, ocular disorders and/or centrally and peripherally mediated hypertension comprising administration to a subject in need thereof an effective amount of a compound of Formula (Ia) as described in the seventh aspect of the present invention.

Embodiments of a tenth aspect of the present invention comprise a method of inhibiting methyltransferase proteins comprising administration of an effective amount of a compound of Formula (Ia) as described in the seventh aspect of the present invention.

DETAILED DESCRIPTION OF THE INVENTION

The description of the invention herein should be construed in congruity with the laws and principals of chemical bonding. An embodiment or aspect which depends from another embodiment or aspect, will describe only the variables having values and provisos that differ from the embodiment or aspect from which it depends. Thus, for example, an embodiment which reads "the compound of formula (I) according to the $n^{th}$ aspect of the invention, wherein W is CH" should be read to include all remaining variables with values defined in the $n^{th}$ aspect and should be read to further include all the provisos, unless otherwise indicated, pertaining to each and every variable in the $n^{th}$ aspect.

As used herein the term "$C_{1-4}$alkyl" may be a straight or branched chain having from 1 to 4 carbon atoms and includes methyl, ethyl, n-propyl, isopropyl, n-butyl, sec-butyl, and tert-butyl. As used herein the term "$C_{1-6}$alkyl" may be a straight or branched chain having from 1 to 6 carbon atoms and includes methyl, ethyl, n-propyl, isopropyl, n-butyl, sec-butyl, tert-butyl, n-pentyl, 2-methylbutyl, n-hexyl, etc. The term "$C_{3-7}$cycloalkyl" are cyclic alkanes with or without branching having from 3 to 7 carbon atoms and includes cyclopropyl, cyclobutyl, cyclopentyl, cyclohexyl, cycloheptyl, 2-methylcyclopropyl etc. The term "$C_{2-3}$alkylene" can be a straight or branched chain having from 2 to 3 carbon atoms and includes —$(CH_2)_2$—, —$(CH_2)_3$—, —$CH(CH_3)$—, —$C(CH_3)_2$—, and —$CH(CH_3)CH_2$—. The term "alk(en)ylene" can mean alkenylene or alkylene. The term "halogen" or "halo" includes fluoro, chloro, bromo and iodo.

It is to be understood that the present invention includes stereoisomers, e.g. optical isomers including individual enantiomers and mixtures of enantiomers which can arise as a consequence of structural asymmetry due to the presence of an asymmetric carbon atom which may be incorporated in some examples of the Formula I compounds. The compounds of the present invention may be prepared enantioselectively, or alternatively, the separation of the individual stereoisomers can be accomplished by application of various methods which are well known to practitioners in the art.

For medicinal use, the pharmaceutically acceptable acid addition salts of Formula (I) compounds are included in the invention. Such salts are those in which the anion does not contribute significantly to toxicity or pharmacologic activity of the organic cation. These salts may be preferred in some cases. The acid addition salts may be prepared from inorganic or organic acids, e.g. salts with acids such as hydrochloric, hydrobromic, hydroiodic, phosphoric, sulfuric, maleic, acetic, citric, succinic, tartaric, benzoic, fumaric, mandelic, p-toluenesulfonic, methanesulfonic, ascorbic, lactic, gluconic, trifluoroacetic and the like. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using using dosage forms well known to those of ordinary skill in the pharmaceutical arts. The compounds can be administered alone but generally will be administered with a pharmaceutical carrier selected upon the basis of the chosen route of administration and standard pharmaceutical practice.

Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

The compounds of this invention can also be administered to the eye, preferably as a topical opthalmic formulation. The opthalmic formulation may be a sterile opthalmic suspension or solution, formed by combining a compound of this invention with opthalmologically acceptable preservatives, surfactants, viscosity enhancers, penetration enhancers, buffers, sodium chloride, and water. Opthalmic solution formulations may be prepared by dissolving a compound of this invention in a physiologically acceptable isotonic buffer which may include an opthalmologically acceptable surfactant to assist in dissolving the compound. The opthalmic solution may also contain an agent to increase viscosity such as hydroxymethylcellulose or a gelling agent such as gellan or xanthan gum. The compounds of this invention can also be combined with a preservative and an appropriate vehicle such as mineral oil or liquid lanolin to provide an opthalmic ointment. Opthalmic gels can be prepared by suspending a compound of this invention in a hydrophilic base such as carbopol-940. The preferred opthalmic formulation is the opthalmic suspension or solution. The opthalmic suspension or solution will contain approximately 0.01% to 5% by weight of a compound of this invention and will have a pH of about 5 to 8. The opthalmic suspension or solution can be topically administered by delivering 1 to 2 drops of the formulation to the surface of the eye. This dosage can be administered between 1 to 4 times daily at the discretion of the clinician.

The dosage can vary within wide limits and will have to be adjusted to the individual requirements in each particular case. By way of general guidance, the daily oral dosage can vary from about 0.01 mg to 1000 mg, 0.1 mg to 100 mg, or 10 mg to 500 mg per day of a compound of Formula (I) or of the corresponding amount of a pharmaceutically acceptable salt thereof. The daily dose may be administered as single dose or in divided doses and, in addition, the upper limit can also be exceeded when this is found to be indicated.

Synthesis

The compounds of Formula I can be synthesized as shown in Schemes 1–3. Specific reactions employed for the preparation of compounds of Formula I are described below. Many of the reactions are conventional and their modification for adaptation for specific compounds of Formula I would be known to one skilled in the art of organic synthesis. It will be understood by one skilled in the art that the functionality present on the molecule should be consistent with the desired transformation and that modification of the order of the synthetic steps may be necessary to prepare a compound of the invention. Preferred methods for the synthesis of Formula I compounds include, but are not limited to, the methods described below. The abbreviations used in the description and examples are conventional abbreviations well-known to those skilled in the art. Some of the abbreviations used are as follows:

| | |
|---|---|
| $CH_2Cl_2$ = | Dichloromethane |
| $CH_3CN$ = | Acetonitrile |
| DMF = | N,N-Dimethylformamide |
| DMSO = | Dimethylsulfoxide |

-continued

| | |
|---|---|
| EtOAc = | Ethyl acetate |
| EtOH = | Ethanol |
| Et$_2$O = | Diethyl ether |
| Fmoc = | (9-Fluorenylmethoxycarbonyl) |
| THF = | Tetrahydrofuran |
| MeOH = | Methanol |
| NMP = | 1-Methyl-2-pyrrolidinone |
| TFA = | Trifluoroacetic acid |
|  = | polystryene support |

Scheme 1

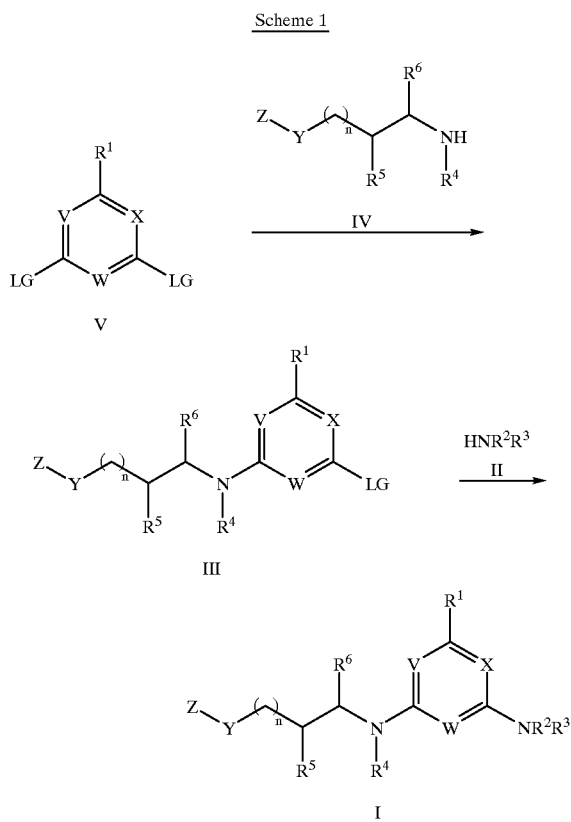

Compounds of Formula I may be prepared, as shown in Scheme 1, by sequential displacement of leaving groups on a heterocycle, V, with appropriate amines, IV and II, in the presence of a base in an appropriate solvent. Examples of useful leaving groups, LG, on heterocycle V include, but are not limited to, Cl, Br, I, alkylsulfonate, arylsulfonate or perhaloalkylsulfonate. Useful bases include, but are not limited to, an excess of the amine itself (IV or 11), metal carbonates such as K$_2$CO$_3$ or CsCO$_3$, hindered alkoxides such as potassium t-butoxide, or non-nucleophilic tertiary organic amines such as triethylamine, N,N-diisopropylethylamine or 4-methylmorpholine. Typical solvents include, but are not limited to, aprotic solvents such as NMP, DMF, dimethylacetamide, CH$_3$CN, dioxane, CH$_2$Cl$_2$, THF or protic solvents such as MeOH, EtOH, isopropanol, butanol, amyl alcohol, cyclohexanol and ethoxyethoxyethanol. The temperature range used for both steps in Scheme 1 is between –10° C. and 200° C. It is understood by one skilled in the art that mixtures of regioisomers of intermediate III may be obtained from the initial displacement reaction in Scheme 1. It is also understood by one skilled in the art that the regioisomers thus obtained can be separated and purified by recrystallization or column chromatography and then further reacted to give compounds of Formula I.

In a more detailed description of the procedure, one molar equivalent of an optionally substituted pyrimidine, such as 4,6-dichloropyrimidine or 2,4-dichloropyrimidine, and one molar equivalent of a tertiary amine such as triethylamine, diisopropylethylamine or 4-methylmorpholine and one molar equivalent of an amine, ZY(CH$_2$)$_n$CH(R$^5$)CH(R$^6$)NH (R$^4$), are combined in a solvent such as EtOH and maintained between –10° C. to 200° C. for a period of 1 to 48 hours. A preferred temperature range for this step is between 0° C. and 80° C.

The reaction mixture can be filtered and the filtrate concentrated under reduced pressure to provide the intermediate product, III. Alternatively, the reaction mixture can be diluted with an organic solvent such as CH$_2$Cl$_2$ or EtOAc. The organic layer can then be washed with water and brine, dried over magnesium sulfate or sodium sulfate, filtered, and concentrated under reduced pressure to provide the intermediate product. The intermediate product may be purified by recrystallization or by chromatography on silica gel using an eluant such as EtOAc, hexanes, CH$_2$Cl$_2$, chloroform, Et$_2$O, MeOH, EtOH or mixtures thereof.

The second step of the synthesis consists of combining one molar equivalent of the intermediate product, III, such as a 2-chloro-4-aminopyrimidine, 4-chloro-2-aminopyrimidine or 4-chloro-6-aminopyrimidine derivative, with either two or more molar equivalents of amine, R$^3$R$^2$NH, or one molar equivalent of amine, R$^3$R$^2$NH, and one molar equivalent of a tertiary amine such as triethylamine, diisopropylethylamine, or 4-methylmorpholine, in a solvent such as NMP or ethoxyethoxyethanol for a period of 1 to 48 hours at reaction temperatures between –10° and 200° C.

The reaction mixture is then allowed to cool to room temperature. In cases where more than two equivalents of amine, R$^3$R$^2$NH, were used, the mixture can be stirred with polystyrene-bound aldehyde resin in order to scavenge the excess amine. (The aldehyde resin was prepared by treating chloromethyl polystyrene resin (Merrifield resin) with 1.4 molar equivalents of sodium bicarbonate in anhydrous DMSO at 160° C. for 24 hours. The resin was then collected by filtration, washed with DMSO, H$_2$O, 1:1 DMSO/H$_2$O, DMF, acetone, EtOH, CH$_2$Cl$_2$, Et$_2$O and MeOH, then was dried under vacuum). The reaction mixture is filtered and the filtrate is concentrated under reduced pressure. The crude material can be purified by either chromatography on silica gel using an eluant such as CH$_2$Cl$_2$, hexane, EtOAc, chloroform, Et$_2$O, MeOH, EtOH or mixtures thereof. Alternatively, the crude material can be purified by reverse phase HPLC on C-18 using eluent such as MeOH, CH$_3$CN, H$_2$O, TFA or mixtures thereof. If necessary, further purification of the compound can be accomplished by recrystallization.

Scheme 2

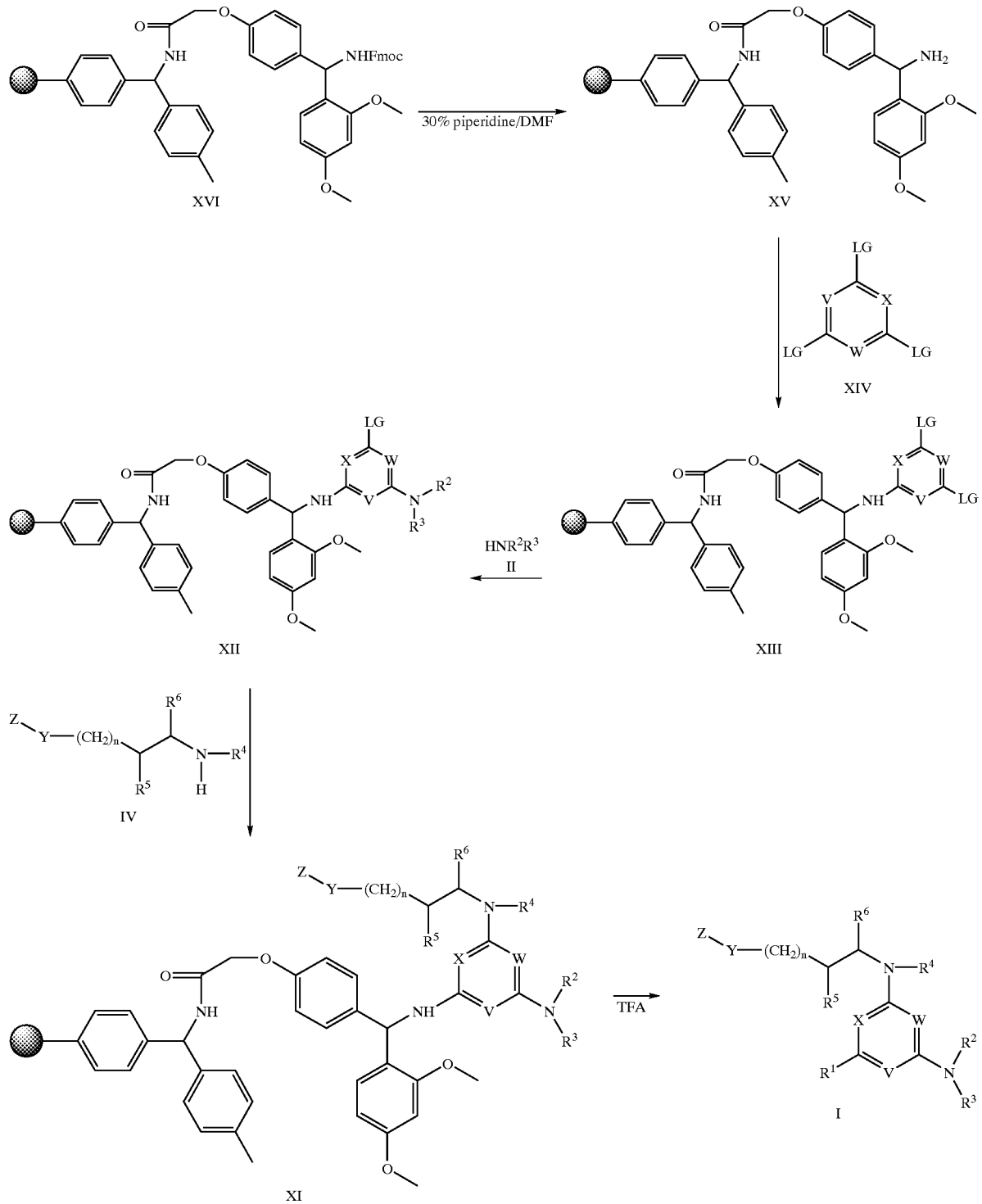

Other compounds of Formula I may be prepared, as shown by Scheme 2, by sequential displacement of leaving groups on a substituted heterocycle, XIV, which has been attached to an insoluble polymer support, XV, with appropriate amines, IV and II, in the presence of a base in an appropriate solvent. Examples of useful leaving groups, LG, on heterocycle XIV include, but are not limited to, Cl, Br, I, alkylsulfonate, arylsulfonate or perhaloalkylsulfonate. Useful bases include, but are not limited to, an excess of the amine itself (IV or II), metal carbonates such as $K_2CO_3$ or $CsCO_3$, or non-nucleophilic tertiary organic amines such as triethylamine, N,N-diisopropylethylamine or 4-methylmorpholine. Typical solvents include, but are not limited to dichloroethane, DMF and NMP and the reactions are typically carried out between 0° C. and 100° C. The resulting resin bound compound, XI, is treated with acid, such as TFA, in an appropriate solvent such as $CH_2Cl_2$, then the resin is filtered and rinsed with solvent. The filtrate and combined rinsing solution is then combined and concentrated under reduced pressure to afford compounds of Formula I wherein $R^1$=$NH_2$.

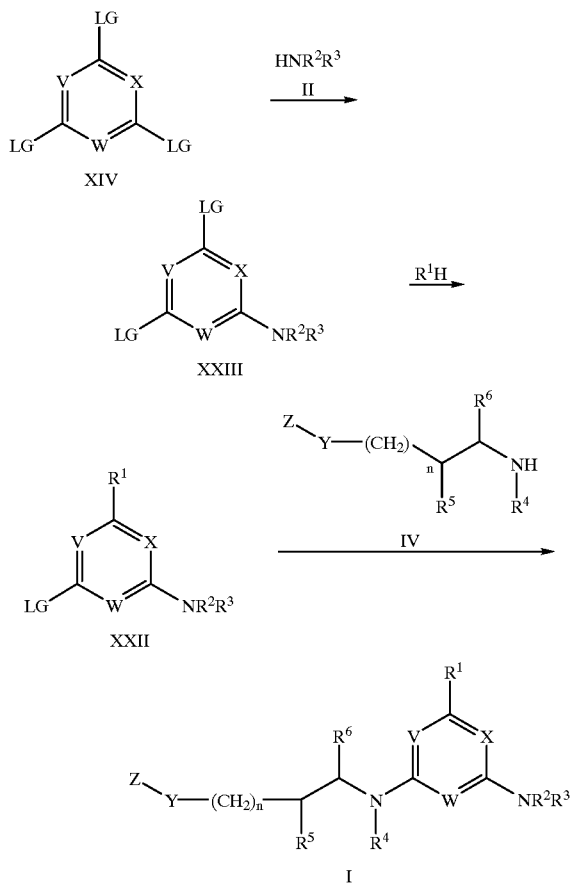

Some compounds of Formula I may be prepared, as shown in Scheme 3, by sequential displacement of leaving groups on a heterocycle, XIV, with appropriate amines, in the presence of base in an appropriate solvent. The leaving groups, solvents, bases, and techniques used for isolating the intermediate products as well as the compounds of Formula I are the same as previously described for Scheme 1.

In a more detailed description of the procedure, one molar equivalent of a heterocycle, XIV, such as cyanuric chloride, and one molar equivalent of a tertiary amine such as triethylamine, diisopropylethylamine, or 4-methylmorpholine, and one molar equivalent of an amine, $R^3R^2NH$, are combined in a solvent such as THF and maintained between −10° C. to 30° C. for a period of 1 to 48 hours. The reaction mixture is concentrated under reduced pressure, the residue is dissolved in a solvent, such as EtOAc or $CH_2Cl_2$, and then extracted with 1 N HCl, $H_2O$, and brine. The organic layer is dried, filtered, and concentrated to afford intermediate, XXIII. Intermediate XXIII can be combined with an amine, $R^1H$, such as ammonium hydroxide, dimethylamine or morpholine in a solvent such as THF in the presence of base at ambient temperature for a period of 1 to 48 hours. The reaction mixture is concentrated under reduced pressure and the residue is dissolved in a solvent such as $CH_2Cl_2$ or EtOAc then extracted with $H_2O$. The organic layer is dried, filtered and concentrated in vacuo to afford intermediate, XXII. Intermediate XXII can be combined with either two or more molar equivalents of amine, $ZY(CH_2)_nCH(R^5)CH(R^6)NH(R^4)$, or one molar equivalent of amine, $ZY(CH_2)_nCH(R^5)CH(R^6)NH(R^4)$, and one molar equivalent of a tertiary amine such as triethylamine, diisopropylethylamine, or 4-methylmorpholine, in a solvent such as THF or NMP at reaction temperatures between approximately 30° C. and 80° C. for 1 to 48 hours. The reaction may then be concentrated under reduced pressure and the residue dissolved in a solvent such as $CH_2Cl_2$ or EtOAc. The organic layer can be extracted with $H_2O$, dried, and concentrated to afford compound of Formula I as the free base. Alternatively, the organic layer can be washed with 1 N HCl and solids which precipitate from the organic layer can be collected by filtration. The solids can be washed with $H_2O$ and $CH_3CN$, triturated with hot $CH_3CN$, collected by filtration, and dried to afford compounds of Formula I as the hydrochloride salt.

The amines, $ZY(CH_2)_nCH(R^5)CH(R^6)NH(R^4)$ and $R^3R^2NH$, employed in the synthesis of Formula I compounds, are either commercially available or can be readily synthesized by the methods shown in Schemes 4–6.

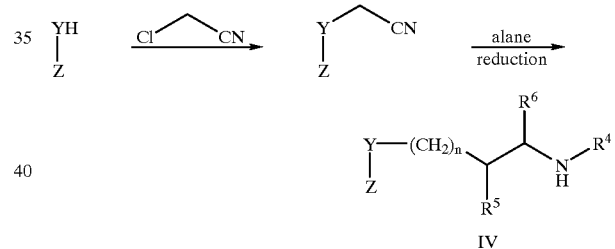

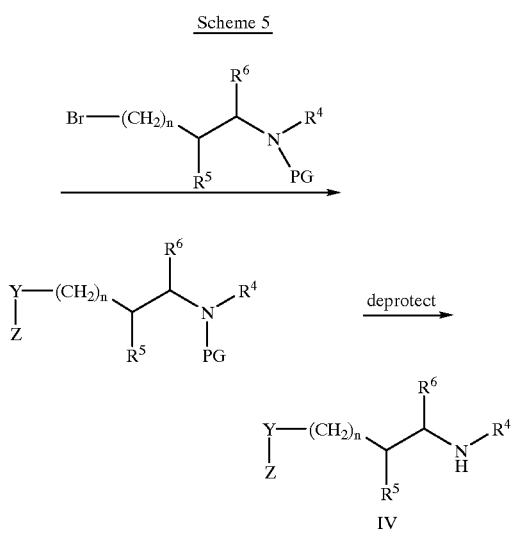

Scheme 6

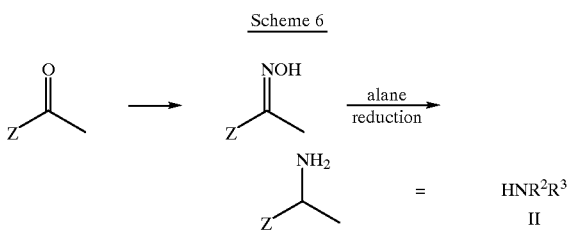

Racemic mixtures of an amine may be resolved by methods known to those skilled in the art and the chiral amine may then be used in the synthesis. A typical preparation of an amine, as shown in Scheme 4, may be accomplished by refluxing an acetonitrile solution of an aniline, phenol, thiophenol or amino, thio or hydroxyl bearing heterocycle with chloroacetonitrile in the presence of a base, such as potassium carbonate. The resulting acetonitrile derivative may then be reduced, with a reducing agent such as alane, to provide an amine of Formula IV wherein n=0, $R^4$, $R^5$, and $R^6$ are H. Alternatively, the amines can be prepared as shown in Scheme 5, by alkylating a substituted aniline, phenol, thiophenol or amino, thio or hydroxyl bearing heterocycle with a protected aminoalkylhalide to provide protected alkylamine derivatives. A preferred protecting group (PG) is the tert-Butoxycarbonyl (Boc) group. These derivatives can then be deprotected to provide amine intermediates of Formula IV. For example, when PG is Boc, treatment of the protected intermediate with an acid such as trifluoroacetic acid or hydrochloric acid provides amines of Formula IV.

A third method used to synthesize amine intermediates is shown in Scheme 6 and consists of the preparation of an oxime which is then reduced to provide the amine intermediate, II.

All of the compounds were synthesized by using the preceding general methodologies and were characterized by LC/MS. The following tables provide retention times and the mass observed for selected compounds of the invention. For LC/MS analysis all Liquid Chromatography (LC) data were recorded on a Shimadzu LC-10AS liquid chromatograph using a SPD-10AV UV-Vis detector and Mass Spectrometry (MS) data were determined with a Micromass Platform for LC in electrospray mode. The various LC/MS methods used for the analysis of the compounds are given below. Purification of compounds by preparative HPLC was accomplished using either a Shimadzu LC-8A liquid chromatograph using a SPD-10AV UV-Vis detector and equipped with FRC-10A fraction collectors or a Varian Prostar Model 215 liquid chromatograph using a Rainin Dynamax UV-Vis detector. A typical preparative HPLC method is given below. In the LC/MS methods and the preparative HPLC method Solvent A is 10% MeOH/90% $H_2O$/0.1% TFA and Solvent B is 90% MeOH/10% $H_2O$/0.1% TFA.

Preparative HPLC Method
Column: YMC ODS S5 30×100 mm
Gradient: Linear gradient from 100% Solvent A/0% Solvent B to 0% Solvent A/100% Solvent B
Gradienttime: 11 minutes
Hold time: 5 minutes
Flow rate: 49 mL/min
Detector Wavelength: 254 nm
LC/MS Method A Column: YMC ODS S5 4.6×50 mm Ballistic
Gradient: Linear gradient from 100% Solvent A/0% Solvent B to 0% Solvent A/100% Solvent B
Gradient time: 3 minutes
Hold time: 1 minute
Flow rate: 4 mL/min
Detector Wavelength: 220 nm
LC/MS Method B
Column: YMC ODS-A S7 3.0×50 mm
Gradient: Linear gradient from 100% Solvent A/0% Solvent B to 0% Solvent A/100% Solvent B
Gradient time: 2 minutes
Hold time: 1 minute
Flow rate: 5 mL/min
Detector Wavelength: 220 nm

TABLE 1

All of the compounds in Table 1 were analyzed using LC/MS Method A.

| Compound # | HPLC Retention Time (min) | MS Data (M + H) + |
|---|---|---|
| 1 | 1.71 | 320 |
| 2 | 2.84 | 295 |
| 3 | 3.09 | 376 |
| 4 | 1.53 | 311 |
| 5 | 1.49 | 306 |
| 6 | 2.29 | 364 |
| 7 | 3.06 | 356 |
| 8 | 3.17 | 399 |
| 9 | 3.26 | 399 |
| 10 | 3.37 | 331 |
| 11 | 1.61 | 306 |
| 12 | 1.79 | 320 |
| 13 | 3.03 | 413 |
| 14 | 2.44 | 414 |
| 15 | 2.99 | 447 |
| 16 | 3.00 | 371 |
| 17 | 3.03 | 385 |
| 18 | 2.69 | 327 |
| 19 | 1.11 | 322 |
| 20 | 1.29 | 322 |
| 21 | 2.77 | 335 |
| 22 | 2.80 | 342 |
| 23 | 3.49 | 324 |
| 24 | 3.25 | 369 |
| 25 | 3.21 | 431 |
| 26 | 3.15 | 383 |
| 27 | 2.94 | 311 |
| 28 | 2.96 | 358 |
| 29 | 3.19 | 325 |
| 30 | 3.30 | 372 |
| 31 | 3.24 | 374 |

TABLE 2

| Compound | HPLC Retention Time (min) | MS Data (M + H)+ | LC/MS Method |
|---|---|---|---|
| 32 | 3.24 | 383 | A |
| 33 | 3.48 | 417 | A |
| 34 | 3.44 | 427 | A |
| 35 | 3.17 | 363 | A |
| 36 | 3.36 | 417 | A |
| 37 | 3.09 | 349 | A |
| 38 | 2.94 | 400 | A |
| 39 | 1.63 | 460 | B |
| 40 | 3.07 | 365 | A |
| 41 | 2.96 | 351 | A |
| 42 | 3.16 | 401 | A |
| 43 | — | 385 | — |
| 44 | 1.57 | 387 | B |
| 45 | 1.49 | 414 | B |

TABLE 2-continued

| Compound | HPLC Retention Time (min) | MS Data (M + H)+ | LC/MS Method |
|---|---|---|---|
| 46 | 1.57 | 387 | B |
| 47 | 1.52 | 432 | B |
| 48 | 3.01 | 353 | A |
| 49 | 3.37 | 363 | A |
| 50 | 3.16 | 369 | A |
| 51 | 3.13 | 367 | A |
| 52 | 3.11 | 379 | A |
| 53 | 3.29 | 403 | A |
| 54 | 3.00 | 365 | A |
| 55 | 2.80 | 360 | A |
| 56 | 3.20 | 385 | A |
| 57 | 3.22 | 339 | A |
| 58 | 1.61 | 414 | B |
| 59 | 1.61 | 414 | B |
| 60 | 3.02 | 335 | A |
| 61 | 3.15 | 353 | A |
| 62 | 3.14 | 369 | A |
| 63 | 3.25 | 367 | A |
| 64 | 3.16 | 353 | A |
| 65 | 3.11 | 349 | A |
| 66 | 3.16 | 413 | A |
| 67 | 3.26 | 367 | A |
| 68 | 3.31 | 431 | A |
| 69 | 3.23 | 383 | A |
| 70 | 3.31 | 431 | A |
| 71 | 3.40 | 403 | A |
| 72 | 3.29 | 349 | A |
| 73 | 2.72 | 351 | A |
| 74 | 1.51 | 398 | B |
| 75 | 1.28 | 396 | B |
| 76 | 1.53 | 398 | B |
| 77 | 1.50 | 410 | B |
| 78 | 1.00 | 395 | B |
| 79 | 1.61 | 394 | B |
| 80 | 1.29 | 426 | B |

TABLE 3

The Formula IV intermediates in Table 3 were analyzed using LC/MS method B.

| Formula IV Intermediate | HPLC Retention Time (min) | MS Data observed m/z |
|---|---|---|
| 3-(2-Fluorophenoxy)propylamine hydrochloride | 0.54 | 170 |
| 3-(3-Fluorophenoxy)propylamine hydrochloride | 0.64 | 170 |
| 3-(4-Fluorophenoxy)propylamine hydrochloride | 0.60 | 170 |
| 3-(2-Methoxyphenoxy)propylamine hydrochloride | 0.63 | 182 |
| 3-(3-Methoxyphenoxy)propylamine hydrochloride | 0.66 | 182 |
| 3-(4-Methoxyphenoxy)propylamine hydrochloride | 0.59 | 182 |
| 3-(2-Cyanophenoxy)propylamine hydrochloride | 0.59 | 177 |
| 3-(3-Cyanophenoxy)propylamine hydrochloride | 0.54 | 177 |
| 3-(4-Cyanophenoxy)propylamine hydrochloride | 0.48 | 177 |
| 2-(2-Cyanophenoxy)ethylamine hydrochloride | 0.45 | 163 |
| 2-(3-Cyanophenoxy)ethylamine hydrochloride | 0.38 | 163 |
| 2-(4-Cyanophenoxy)ethylamine hydrochloride | 0.31 | 163 |
| 2-(2-Pyridinyl)ethylamine dihydrochloride | 0.11 | 139 |
| 2-(3-Pyridinyl)ethylamine dihydrochloride | 0.09 | 139 |
| 2-(4-Pyridinyl)ethylaminedi hydrochloride | 0.08 | 139 |

EXAMPLES

The following examples illustrate the invention, but are not intended as a limitation thereof. In the following examples, all temperatures are given in degrees Centigrade. Melting points were determined on an electrothermal apparatus and are not corrected. Proton nuclear magnetic resonance ($^1$H NMR) spectra were recorded on a Bruker AM-300 or a Varian Gemini 300 spectrometer. All spectra were determined in $CDCl_3$, $DMSO-d_6$, $CD_3OD$ or $D_2O$ unless otherwise indicated. Chemical shifts are reported in • units relative to tetramethylsilane (TMS) or a reference solvent peak and interproton coupling constants are reported in Hertz (Hz). Splitting patterns are designated as follows: s, singlet; d, doublet; t, triplet; q, quartet; m, multiplet; br, broad peak; dd, doublet of doublets; dt, doublet of triplets; and app d, apparent doublet, b broad, etc. Mass spectra were recorded on a Kratos MS-50 or a Finnegan 4500 instrument utilizing direct chemical ionization (DCI, isobutene), fast atom bombardment (FAB), or electron ion spray (ESI).

Analytical thin-layer chromatography (TLC) was carried out on precoated silica gel plates (60F-254) and visualized using UV light, iodine vapors, and/or staining by heating with methanolic phosphomolybdic acid. Column chromatography, also referred to as flash chromatography, was performed in a glass column using finely divided silica gel at pressures somewhat above atmospheric pressure.

A. Synthesis of Intermediates

Example 1

Example of Scheme 6

Preparation of 1-(4-Chlorophenyl)ethylamine (Intermediate of Formula II)

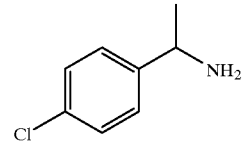

To a mixture of 4'-chloroacetophenone (15.5 g, 100 mmol) and hydroxylamine sulfate (24.6 g, 300 mmol) in EtOH (150 mL) was added 50% (w/w) aqueous NaOH (24 g, 300 mmol) and $H_2O$ (50 mL). The mixture was refluxed for 4 h then was diluted with $H_2O$ (400 mL) and allowed to cool. The mixture was extracted with $CH_2Cl_2$. The organic layers were dried over sodium sulfate, filtered and concentrated under reduced pressure to provide the oxime intermediate as a white solid (16.5 g, 98%). The oxime intermediate was reduced with alane [generated from lithium aluminum hydride (31.0 g, 817 mmol) and sulfuric acid (40.1 g, 409 mmol) by the method of Brown in Fieser and Fieser, Vol 1, 35] in THF at reflux for 6 h, and after the standard workup according to Fieser and Fieser, Vol 1, 584; provided the titled compound (12 g).

Example 2

2-(4-Fluorophenoxy)ethylamine (Intermediate of Formula IV)

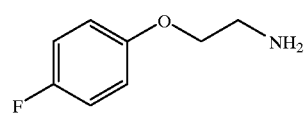

The 2-(4-Fluorophenoxy)ethylamine was prepared by both the method of Scheme 4 and Scheme 5.

Example of Scheme 4

A mixture of 4-fluorophenol (22.4 g, 200 mmol), chloroacetonitrile (17.1 g, 220 mmol) and excess powdered potassium carbonate was refluxed for 7 h then the mixture was concentrated under reduced pressure. The residue was mixed with H₂O and was extracted with Et₂O. The combined organic layers were dried, filtered and concentrated under reduced pressure. The residue was Kugelrohr distilled to provide 2-(4-Fluorophenoxy)acetonitrile (25 g, 84%). The 2-(4-Fluorophenoxy)acetonitrile (25 g, 185 mmol) was reduced with alane [generated from lithium aluminum hydride (19.6 g, 516 mmol) and sulfuric acid (25.3 g, 258 mmol) according to the procedure in Example 1]. The crude product was purified by Kugelrohr distillation to provide the titled compound (12 g).

Example of Scheme 5

A mixture of 4-fluorophenol (2.2 g, 20 mmol), 2-Bromo-N-(t-butoxycarbonyl)ethylamine (4.5 g, 20 mmol) and excess powdered potassium carbonate in CH₃CN was refluxed for 48 h then was allowed to cool. The mixture was filtered and the filtrate was concentrated under reduced pressure. The residue was dissolved in Et₂O and was washed with 1 N NaOH. The organic layer was then concentrated under reduced pressure. The residue was stirred in 2N HCl for 16 h at ambient temperature then the mixture was made basic. The mixture was then extracted with Et₂O. The organic layer was dried, filtered and concentrated under reduced pressure to provide the titled compound (1.5 g)

2-(4-Fluorophenoxy)ethylamine, hydrochloride: was prepared by treating a CH₃CN solution of 2-(4-Fluorophenoxy) ethylamine hydrochloric acid then concentrating under reduced pressure. ¹H NMR (dmso-d₆) δ 8.46 (b s, 3H), 7.11(dd, J=9, 9, 2H), 7.00 (dd, J=9, 4, 2H), 4.18 (t, J=5, 2H), 3.16 (t, J=5, 2H).

Example 3

The following intermediates of Formula IV were prepared according to the method of Scheme 4 as in Example 2.

2-(2-Fluorophenoxy)ethylamine, hydrochloride: ¹H NMR (dmso-d₆) δ 8.35 (b s, 3H), 7.12–7.28 (m, 3H), 6.96–7.03 (m, 1H), 4.28 (t, J=5, 2H), 3.21 (t, J=5, 2H).

2-(3-Fluorophenoxy)ethylamine, hydrochloride: ¹H NMR (dmso-d₆) δ 8.25 (b s, 3H), 7.35 (q, J=8, 1H), 6.78–6.89 (m, 3H), 4.20(t, J=5, 2H), 3.19 (t, J=5, 2H).

2-(3-Methoxyphenoxy)ethylamine, hydrochloride: ¹H NMR (dmso-d₆) δ 8.36 (b s, 3H), 7.21 (dd, J=8, 8,1H), 6.56 (d, J=8, 1H), 6.55 (d, J=8, 1H), 6.53 (s, 1H), 4.18 (t, J=5, 2H), 3.73 (s, 3H), 3.16 (t, J=5, 2H).

2-(4-Methoxyphenoxy)ethylamine, hydrochloride: ¹H NMR (dmso-d₆) δ 8.27 (b s, 3H), 6.94 (d, J=9, 2H), 6.87 (d, J=9, 2H), 4.11 (t, J=5, 2H), 3.70 (s, 3H), 3.15 (b s, 2H).

Example 4

Example of Scheme 1

4-Chloro-r2-(2-phenylethyl)amino]pyrimidine and 2-Chloro-[4-(2-phenylethyl)amino]pyrimidine (Intermediates of Formula III)

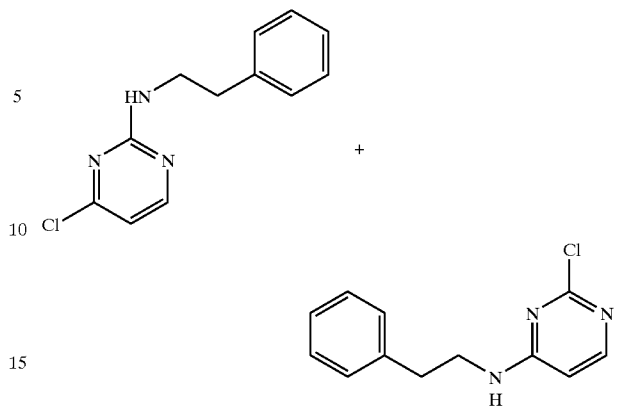

To a solution of 2,4-dichloropyrimidine (750 mg, 5.0 mmol) and triethylamine (0.7 mL, 5.0 mmol) in EtOH (5 mL) was added a solution of 2-phenylethylamine (606 mg, 5.0 mmol) in EtOH (10 mL). The reaction mixture was stirred at rt for 24 h then was diluted with CH₂Cl₂. The organic layer was washed with H₂O and brine, dried over magnesium sulfate, filtered and concentrated under reduced pressure to afford an oil. The crude oil was purified by column chromatography on silica gel (eluted with EtOAc/Hexane, 30/70) to afford 4-chloro-[2-(2-phenylethyl)amino] pyrimidine [200 mg, 17%, (Rf=0.55, SiO₂ eluted with EtOAc/Hexane, 30/70); ¹H NMR (CDCl₃) δ 8.14 (d, J=5, 1H), 7.21–7.35 (m, 5H), 6.57 (d, J=5, 1H), 5.31 (bs, 1H), 3.71 (q, J=7, 2H), 2.92 (t, J=7, 2H); LC/MS (ESI⁺) 233.8 obs] and 2-chloro-[4-(2-phenylethyl)amino]pyrimidine [685 mg, 59%, (R$_f$=0.33, SiO₂ eluted with EtOAc/Hexane, 30/70); ¹H NMR (CDCl₃) δ 8.01 (bs, 1H), 7.20–7.36 (m, 5H), 6.24 (dd, J=2,4, 1H), 5.34 (bs, 1H), 3.64 (bs, 2H), 2.94 (t, J=7, 2H); LC/MS (ESI⁺) 233.8 obs]. A small portion of 4-chloro-[2-(2-phenylethyl)amino]pyrimidine was recrystallized from diisopropyl ether to obtain crystalline material as colorless plates. A single 0.05×0.30×0.30 mm crystal was subjected to X-ray crystallography on a Bruker AXS and the structure was found to be 4-chloro-[2-(2-phenylethyl) amino]pyrimidine.

Example 5

Example of Scheme 1

4-Chloro-2-[(2-(4-fluorophenoxy)ethyl)amino]pyrimidine and 2-Chloro-4-[(2-(4-fluorophenoxy)ethyl] aminolpyrimidine (Intermediates of Formula III)

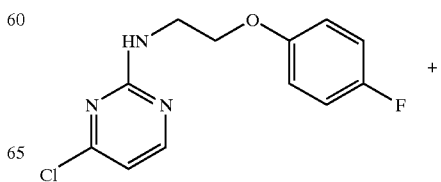

-continued

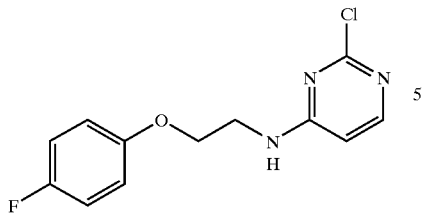

The titled compounds were prepared according to the method of Example 4 starting from 2,4-dichloropyrimidine and 2-(4-fluorophenoxy)ethylamine to afford the titled compounds as white solids. 4-Chloro-2-[(2-(4-fluorophenoxy) ethyl)amino]pyrimidine $^1$H NMR (CDCl$_3$) δ 8.16 (d, J=5, 1H), 6.96 (m, 2H), 6.86 (m, 2H), 6.61 (d, J=5, 1H), 5.82 (bs, 1H), 4.10 (t, J=5, 2H), 3.85 (q, J=5, 2H); MP 85–86° C. 2-Chloro-4-[(2-(4-fluorophenoxy)ethyl)amino]pyrimidine: $^1$H NMR (CDCl$_3$) δ 8.03 (d, J=5, 1H), 6.97 (m, 2H), 6.86 (m, 2H), 6.33 (d, J=6, 1H), 5.60 (bs, 1H), 4.11 (t, J=5, 2H), 3.82 (bs, 2H); MP 143–144° C.

Example 6

Example of Scheme 1

6-Chloro-4-[(1S)-(1-phenylethyl)amino]pyrimidine (Intermediate of Formula III)

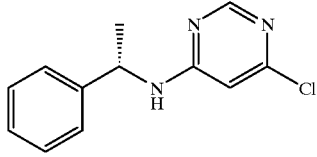

A solution of 4,6-dichloropyrimidine (14.9 g, 100 mmole) and (1S)-1-phenylethylamine (13.3 g, 110 mmole) in CH$_3$CN (100 mL) was refluxed for 4 hours. The reaction was partitioned between Et$_2$O (500 mL) and H$_2$O (250 mL). The organic layer was dried over sodium sulfate, filtered and concentrated under reduced pressure. The residue was purified by flash chromatography on silica gel 60 with Hexane/ EtOAc 3:1. Pure fractions were combined, concentrated under reduced pressure, and dried under high vacuum to afford the titled compound (18.6 g, 80%) as a yellow oil. $^1$H NMR (CDCl$_3$): δ 1.57 (d, J=7.0 Hz, 3H), 4.6 (b s,1H), 5.6 (b s,1H), 6.19 (s,1H), 7.34 (m, 5H), 8.30 (s,1H); LC/MS (MH+) 233.62.

Example 7

Example of Scheme 2
Intermediate XV

Knorr resin, XVI, (25 g, 20 mmol) was shaken in DMF (150 mL) for 5 minutes and drained. The swollen resin was treated with 30% piperidine in DMF (150 mL) and shaken at ambient temperature for 25 minutes. The resin was then drained and washed sequentially with DMF and CH$_2$Cl$_2$ (4×200 mL each) and dried under vacuum at ambient temperature to yield resin XV.

Example 8

Example of Scheme 2

Intermediate XIII of structure:

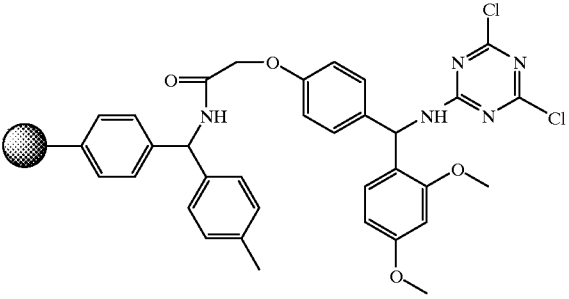

To resin XV was added diisopropylethylamine (17.4 mL, 100 mmol) and a solution of cyanuric chloride [XIV, wherein V, W, X are N and LG is Cl (36.9 g, 200 mmol)] in dichloroethane (250 mL). The mixture was shaken for 1 h, drained, and washed sequentially with DMF and CH$_2$Cl$_2$ (4×200 mL each). The resin was then dried under vacuum at ambient temperature to yield resin XIII.

Example 9

Example of Scheme 2

Intermediate XII of structure:

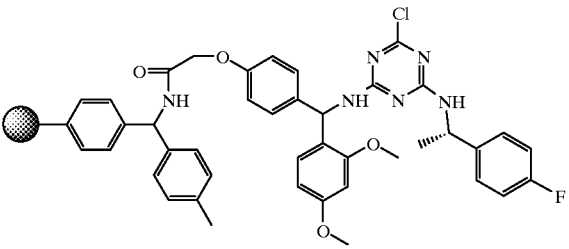

To Intermediate XIII, Compound of Example 8, (20 mmol) in NMP (300 mL) was added 1-[(1S)-(4-fluorophenyl)ethyl]amine, 11 (3.06 g, 22 mmol) and diisopropylethylamine (2.59 g, 20 mmol). The mixture was shaken at 40° C. for 18 h, drained, and washed sequentially with DMF, THF, CH$_2$Cl$_2$, and MeOH (4×200 mL each). Drying under vacuum at ambient temperature afforded a pale tan free flowing resin of formula XII, above.

Example 10

Example of Scheme 2
Intermediate XII of Structure:

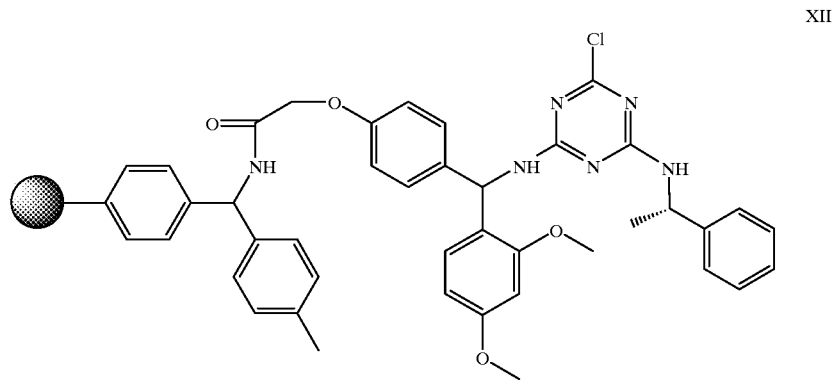

To Intermediate XIII, Compound of Example 8, (8.0 g, 6.4 mmol) in NMP (60 mL) was added [(1S)-1-(phenylethyl)]amine (1.0 mL, 7.6 mmol) and diisopropyl-ethylamine (1.12 mL, 6.4 mmol). The mixture was vortexed (100 rpm) at 40° C. for 16 hours. The solution was drained, then the resin was washed sequentially with DMF (3×50 mL), THF (3×50 mL), $CH_2Cl_2$ (3×50 mL) and MeOH (3×50 mL) and dried to provide XII, above.

Example 11

Example of Scheme 2
Intermediate XI of structure:

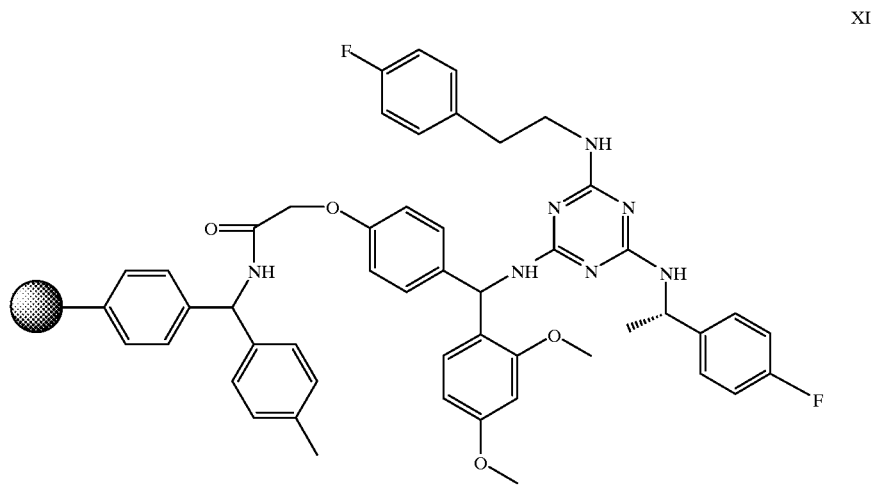

Intermediate XI was synthesized in a 48 tube reactor shaker. To a reaction tube containing Intermediate XII, Compound of Example 9, (0.100 g, 90 μmoles), was added 2-(4-fluorophenyl)ethylamine, IV (0.9 mL, 450 μmoles as a 0.5 M solution in NMP). The reactor was shaken at 80° C. for 4 days, drained, and the resin washed sequentially with DMF, THF, CH$_2$Cl$_2$, and MeOH (4×2 mL each) to provide the Intermediate XI above.

Example 12

Example of Scheme 2

Intermediate XI of structure:

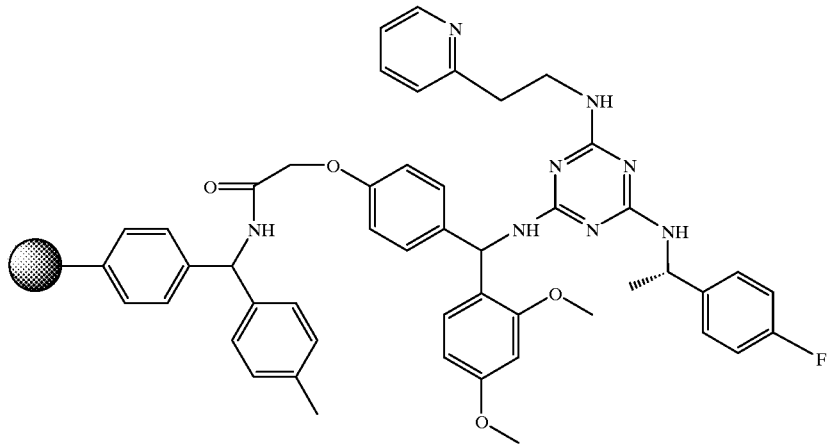

XI

Intermediate XI (above) was prepared from Intermediate XII, Compound of Example 9, (0.100 g, 90 μmoles) and 2-(2-aminoethyl) pyridine (0.9 mL, 450 μmoles as a 0.5 M solution in NMP) as described previously for Example 11.

Example 13

Example of Scheme 2

Intermediate XI of structure:

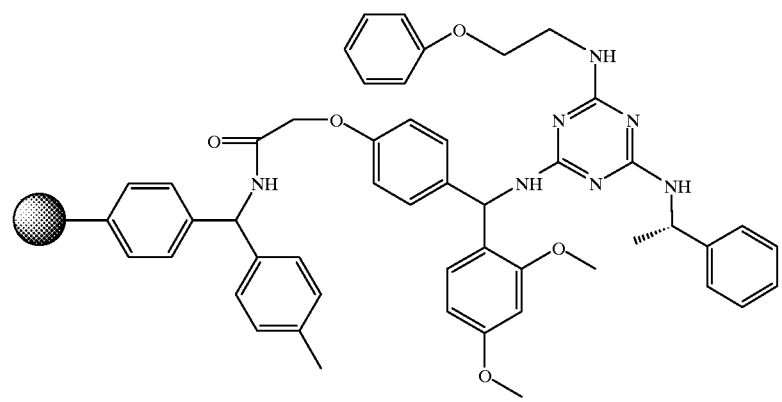

XI

To Intermediate XII, Compound of Example 10, (5.5 g, 4.4 mmol) in NMP (40 mL) was added 2-phenoxyethylamine (4.83 g, 35.2 mmol). The mixture was vortexed (100 rpm) at 85° C. for 72 h then the solution was drained. The resin was washed sequentially with DMF (3×50 mL), THF (3×50 mL), CH$_2$Cl$_2$ (3×50 mL) and MeOH (3×50 mL) then dried to provide Intermediate XI, above.

Example 14

Example of Scheme 3

4,6-Dichloro-$N^2$-[(1S)-1-phenylethyl]-1,3,5-triazine-2-amine (Intermediate of Formula XXIII)

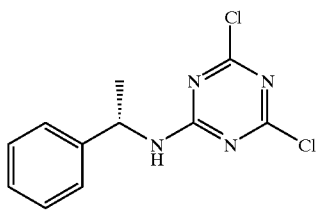

To a solution of cyanuric chloride (25.0 g, 0.135 mol), diisopropylethylamine (17.5 g, 0.135 mol) in THF (500 mL) at 0° C. was added dropwise a solution of (1S)-1-phenylethylamine (16.4 g, 0.135 mol) in THF (100 mL) while maintaining the reaction temperature at or near 0° C. The reaction mixture was allowed to warm to ambient temperature then was concentrated under reduced pressure. The residue was dissolved in EtOAc (500 mL) and extracted with 1 N HCl (250 mL), $H_2O$ (250 mL) and brine (250 mL). The organic layer was dried over sodium sulfate, filtered and concentrated under reduced pressure to afford the titled compound as a white solid (35 g, 96%) MP 146–147° $^1$H NMR (CDCl$_3$) δ 7.39 (m, 5H), 6.40 (b d, 1H), 5.25 (m, 1H), 1.59 (d, 3H); MS (ESI$^+$) (M$^+$) 269.1 obs.

Example 15

Example of Scheme 3

4-Chloro-$N^2$-r(1S)-1-henylethyll-1,3,5-triazine-2,4-diamine (Intermediate of Formula XXII)

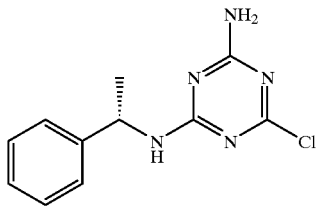

To a solution of 4,6-Dichloro-$N^2$-[(1S)-1-phenylethyl]-1,3,5-triazine-2-amine, (Compound of Example 14), in THF (500 mL) was added conc. NH$_4$OH (50 mL). The reaction mixture was stirred at ambient temperature for 48 h then was concentrated under reduced pressure. The residue was dissolved in CH$_2$Cl$_2$ (500 mL) and was washed with H$_2$O (2×250 mL). The organic layer was filtered through a cotton plug then dried over sodium sulfate, filtered and concentrated under reduced pressure to afford 4-Chloro-$N^2$-[(1S)-1-phenylethyl]-1,3,5-triazine-2,4-diamine as a white solid (29.7 g, 90%) MP 163–164° C., $^1$H (CDCl$_3$) δ 7.78 (m, 5H), 6.1–6.2 (m, 4H), 1.52 (d, 3H), MS (ESI$^+$) (M$^+$) 249.7 obs.

B. Synthesis of Formula I Products

Example 16

Example of Scheme 1

$N^4$-[2-(4-Fluorophenoxy)ethyl]-$N^6$-[(1S)-(1-phenylethyl)]pyrimidine-4,6-diamine

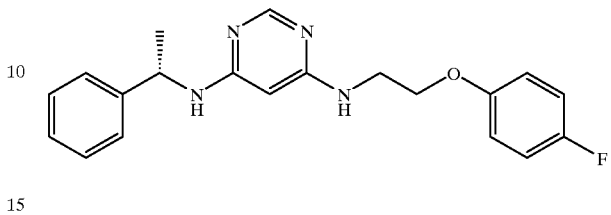

4-[(1S)-(1-phenylethyl)amino]-6-chloropyrimidine, (Intermediate III, Compound of Example 6), (234 mg, 1.0 mmole) and [2-(4-fluorophenoxy)ethyl]amine (357 mg, 2.3 mmole) were combined in a 2 mL pressure vial which was then securely capped. The vial was heated at 150° C. for 20 hours. After cooling, the solid mass was dissolved in CH$_2$Cl$_2$ (25 mL) and extracted with saturated sodium carbonate (25 mL). The organic layer was dried over sodium sulfate and concentrated under reduced pressure. The residue was recrystallized from CH$_2$Cl$_2$ (5 mL) to afford the titled compound as a white solid (191 mg, 54%). $^1$H NMR (CDCl$_3$) δ 1.54 (d, J=6.6 Hz, 3H), 3.54 (q, J=5.5 Hz, 2H), 3.94 (t, J=5.5 Hz, 2H), 4.59 (p, J=6.6 Hz, 1H), 5.05 (broad m, 1H), 5.08 (s, 1H), 5.34 (broad d,1H), 6.77 (m, 2H), 6.95 (t, J=9.1 Hz, 2H), 7.23 (m,1H), 7.32 (d, J=4.4 Hz, 4H), 8.09 (s, 1H), LC/MS (MH$^+$) m/e 353.79 obs.

Example 17

Example of Scheme 2

$N^2$-[(1S)-1-(4-Fluorophenyl)ethyl1-$N^4$-[2-(4-fluorophenyl)ethyl]-1,3,5-triazine-2,4,6-triamine, TFA Salt

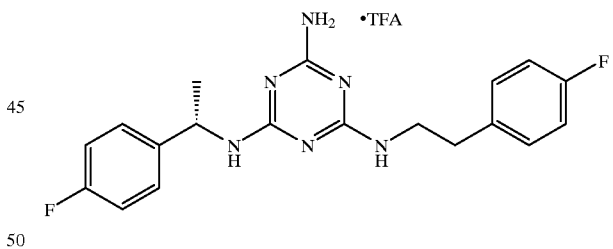

To the Intermediate XI, Compound of Example 11 was added 50% TFA in dichloroethane (1 mL). The mixture was shaken at ambient temperature for 0.5 h, drained into a custom microtube, rinsed with dichloroethane (0.5 mL), and concentrated by centrifugal evaporation to afford the titled compound (74 mg) as a thick amber oil. HPLC-MS (C-18, MeOH/H$_2$O/TFA linear gradient elution, 5 ml/min, 220 nm): product peak (70%) at 1.61 minutes; MS (ESI$^+$) obsd m/z=371.21.

Example 18

Example of Scheme 2

$N^2$-[(1S)-1-(4-Fluorophenyl)ethyl]-$N^4$-[2-(2-pyridinyl)ethyl]-1,3,5-triazine-2,4,6-triamine, TFA Salt

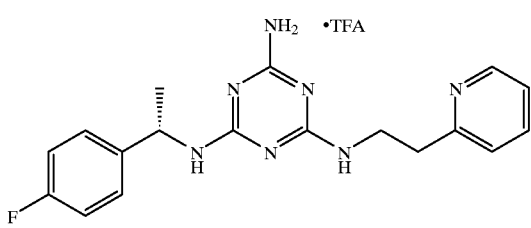

The titled compound was prepared from Intermediate XI, Compound of Example 12 and 50% TFA in dichloroethane (1 ml) as described in Example 17 to afford the titled product (128 mg) as a thick amber oil. HPLC-MS (C-18, MeOH/H$_2$O/TFA linear gradient elution, 5 ml/min, 220 nm): product peak (80%) at 0.93 minutes; MS (ES$^+$) obsd m/z=354.24.

Example 19

Example of Scheme 2, Compound 41
N$^2$-(2-Phenoxyethyl)-N$^4$-[(1S)-1-phenylethyl]-1,3,5-triazine-2,4,6-triamine, TFA salt

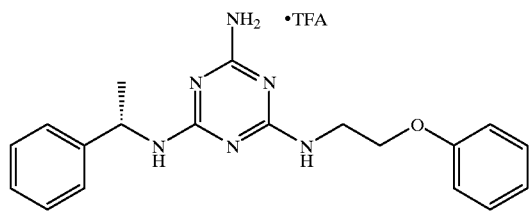

The Intermediate XI, Compound of Example 13, was treated with 50% TFA in CH$_2$Cl$_2$ (50 mL) and the mixture was vortexed for 1 hour. The resin was filtered and was rinsed with CH$_2$Cl$_2$ (2×50 mL). The filtrate and CH$_2$Cl$_2$ rinses were combined and concentrated under reduced pressure to afford the titled compound as a reddish oil (1.1 g).

Example 20

Example of Scheme 3, Compound 41
N$^2$-[2-(2-Phenoxyethyl]-N$^4$-[(1S)-1-phenylethyl]-1,3,5-triazine-2,4,6-triamine, hydrochloride

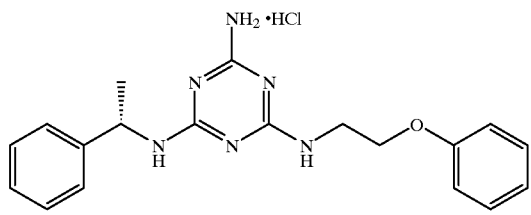

A solution of 4-Chloro-N$^2$-[(1S)-1-phenylethyl]-1,3,5-triazine-2,4-diamine, Compound of Example 15, (15.0 g, 0.056 mol), 2-phenoxyethylamine (8.6 g, 0.062 mol), diisopropylethylamine (25 mL, 0.178 mol) in THF (500 mL) was refluxed for 24 h, then allowed to cool to ambient temperature and concentrated under reduced pressure. The amber residue was dissolved in CH$_2$Cl$_2$ and was washed with 1 N HCl (300 mL). Product precipitated from the organic layer was collected by filtration, washed with H$_2$O and CH$_3$CN, and dried. The product was then triturated in hot CH$_3$CN, collected by filtration and dried to afford the titled compound (18.2 g, 88%) as a white solid. MP 207–208° C., $^1$H NMR (CDCl$_3$) δ 7.19–7.3 (m, 7H), 6.91–6.96 (m, 3H), 5.16–6.08 (b m, 3H), 4.90 (b s, 2H), 3.32–4.04 (m, 4H), 1.49 (d, 3H); MS (ESI$^+$) (M+H)$^+$ 351.2 obs; C, H, N Calc'd. for C$_{19}$H$_{22}$N$_6$O$_1$.HCl C, 58.98:H, 5.99: N, 21.72; Found C, 59.02:H, 5.87: N, 21.67.

Example 21

Example of Scheme 3
N$^2$-[(1S)-1-(4-Fluorophenyl)ethyl]-N$^4$-[2-(2-pyridinyl)ethyl]-1,3,5-triazine-2,4,6-triamine, dihydrochloride salt

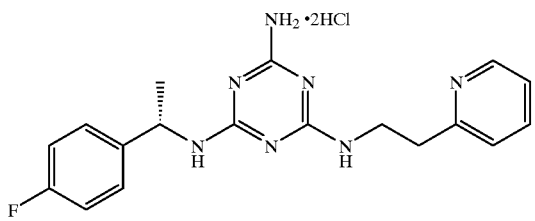

The 4-Chloro-N$^2$-[(1S)-1-(4-fluorophenyl)ethyl]-1,3,5-triazine-2,6-diamine used was prepared from (1S)-1-(4-Fluorophenyl)ethylamine (resolved by the procedure of Takenaka, S. et al. J. Chem. Soc., Perkins Trans. 2 1978, 95–99), cyanuric chloride and ammonium hydroxide according to the procedure outlined in the first two steps of Scheme 3 and by the procedure as described in Examples 14 and 15. A stirred solution of 4-Chloro-N$^2$-[(1S)-1-(4-fluorophenyl)ethyl]-1,3,5-triazine-2,6-diamine (1.15 g, 4.30 mmol), 2-(2-aminoethyl)pyridine (0.58 g, 4.73 mmol), diisopropylamine (20 ml), and THF (10 ml) was heated at reflux for 18 hours and then concentrated under reduced pressure. The yellow residue was taken up in CH$_2$Cl$_2$ and washed with H$_2$O and brine, dried over sodium sulfate, filtered and concentrated under reduced pressure. The residue was chromatographed on silica, eluting with 3% MeOH/CH$_2$Cl$_2$ to afford N$^2$-[(1S)-1-(4-Fluorophenyl)ethyl]-N$^4$-[2-(2-pyridinyl)ethyl]-1,3,5-triazine-2,4,6-triamine (free base) as a pale tan foam (1.10 g, 72%). $^1$H NMR (CDCl$_3$) δ 8.51 (s, 1H), 7.56 (t, 1H), 7.31 (s, 2H), 7.08 (m, 1H), 6.97 (m, 3H), 5.88–5.44 (b m, 1H), 5.42–5.19 (b m, 1H), 5.15 (m, 1H), 4.95 (b s, 2H), 3.72 (d, 2H), 3.20–2.81 (b m, 2H), 1.47 (d, 3H). HPLC-MS (C-18, MeOH/H$_2$O/TFA linear gradient elution, 5 ml/min, 220 nm): 1 peak at 0.84 minutes; MS (ES+) obs. m/z 353.83. A stirred solution of N$^2$-[(1S)-1-(4-Fluorophenyl)ethyl]-N$^4$-[2-(2-pyridinyl)ethyl]-1,3,5-triazine-2,4,6-triamine was treated with 10 mL of 1 N HCl in Et$_2$O and allowed to stand at ambient temperature for 30 minutes. The mixture was concentrated by rotary evaporation to afford the titled compound as a pale white fine powder. LC/MS (C-18, MeOH/H$_2$OTFA linear gradient elution, 5 ml/min, 220 nm): 1 peak at 0.86 minutes; MS (ES+) obsd m/z=354.26. MP=161° C.

Compounds of Formula (Ia) may be prepared as follows:

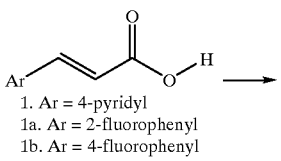

1. Ar = 4-pyridyl
1a. Ar = 2-fluorophenyl
1b. Ar = 4-fluorophenyl

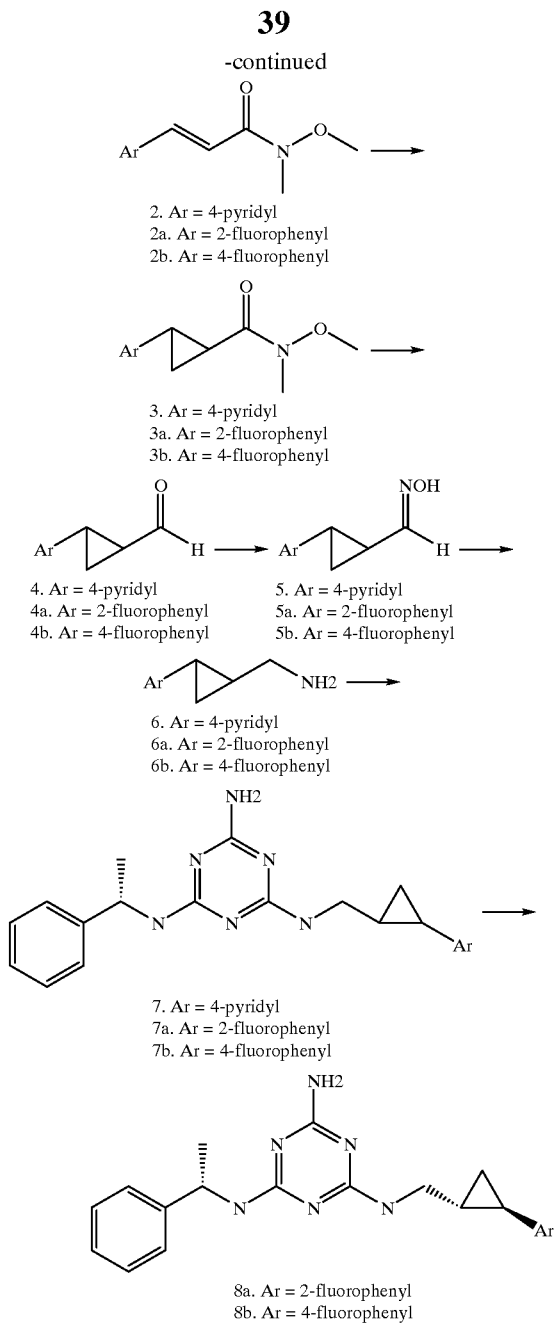

2. Ar = 4-pyridyl
2a. Ar = 2-fluorophenyl
2b. Ar = 4-fluorophenyl

3. Ar = 4-pyridyl
3a. Ar = 2-fluorophenyl
3b. Ar = 4-fluorophenyl

4. Ar = 4-pyridyl
4a. Ar = 2-fluorophenyl
4b. Ar = 4-fluorophenyl

5. Ar = 4-pyridyl
5a. Ar = 2-fluorophenyl
5b. Ar = 4-fluorophenyl

6. Ar = 4-pyridyl
6a. Ar = 2-fluorophenyl
6b. Ar = 4-fluorophenyl

7. Ar = 4-pyridyl
7a. Ar = 2-fluorophenyl
7b. Ar = 4-fluorophenyl

8a. Ar = 2-fluorophenyl
8b. Ar = 4-fluorophenyl

Compound 2

A mixture of compound 1 (10 g, 68 mmol) and $SOCl_2$ (100 mL) in $CH_2Cl_2$ (68 mL) was refluxed for 3 h. After concentration, the residue was dissolved in $CH_2Cl_2$ (100 mL) followed by addition of a suspension of MeONHMe·HCl (10 g, 102 mmol) in $Et_3N$ (20 g) at 0° C. The resulting mixture was allowed to warm to room temperature and stirred for 1 h. The reaction was quenched with water. The organic layer was washed with brine and dried over $MgSO_4$, concentrated to give 2 (11 g, 84%) as a solid which was used in the next step without purification. $^1H$ NMR (300 MHz, $CDCl_3$) δ 3.31 (s, 3H), 3.77 (s, 3H), 7.21 (d, 1H, J=15.9 Hz), 7.41 (d, 2H, J=6.0 Hz), 7.66 (d, 1H, J=15.9 Hz), 8.64 (d, 2H, J=6.0 Hz).

Compound 2a

The title compound was prepared by the general procedure described in 2 using 1a (10 g, 66 mmol). Concentration gave 2a (12.51 g, 99%) as an oil. $^1H$ NMR (300 MHz, $CDCl_3$): δ 3.41 (s, 3H), 3.86 (s, 3H), 7.27–7.15 (m, 3H), 7.70–7.64 (m, 1H), 7.93 (d, 1 h, J=16.0 Hz). MS (ESI) $(M+H)^+$ 209.61.

Compound 2b

The title compound was prepared by the general procedure described in 2 using 1b (10 g, 66 mmol). Concentration gave 2b (12.50 g, 99%) as an oil. $^1H$ NMR (300 MHz, CDCl3): δ 3.27 (s, 3H), 3.73 (s, 3H), 6.93 (d, 1H, J=15 Hz), 7.00–7.07 (m, 2H), 7.49–7.55 (m, 2H), 7.66 (d, 1H, J=15 Hz). MS (ESI) $(M+H)^+$ 209.61.

Compound 3

NaH (2.4 g, 100 mmol) was added to a suspension of trimethylsulfoxonium iodide (22 g, 100 mmol) in DMF (100 mL) at 0° C. The resulting mixture was allowed to warm to room temperature and stirred for 0.5 h. A solution of compound 2 (9 g, 50 mmol) was added to the above reaction mixture at 0° C. The resulting reaction was allowed to warm to room temperature and stirred for 1 h. The reaction was quenched with water and extracted with $CH_2Cl_2$. The organic layer was washed with brine, dried over $MgSO_4$, and concentrated to give a reside. The residue was purified by flash chromatography over silica gel (elution with 2% methanol in ethyl acetate) to give compound 3 (2.1 g, 20%) as an oil.

Compound 3a

The title compound was prepared by the general procedure described in 3 using 2a (12.5 g, 60 mmol). Purification on silica gel gave 3a (2.8 g, 21%) as an oil. $^1H$ NMR (300 MHz, $CDCl_3$): δ 1.35–1.29 (m, 1H), 1.63–1.57 (m, 1H), 2.46–2.36 (m, 1H), 3.22 (s, 3H), 3.69 (s, 3H), 7.06–6.95 (m, 3H), 7.19–7.10 (m, 1H). MS (ESI)$(M+H)^+$ 224.25.

Compound 3b

The title compound was prepared by the general procedure described in 3 using 2b (12.5 g, 60 mmol). Purification on silica gel gave 3b (12.7 g, 95%) as an oil. $^1H$ NMR (300 MHz, CDCl3): δ 1.19–1.25 (m, 1H), 1.54–1.60 (m, 1H), 2.25–2.37 (m, 1H), 2.41–2.49 (m, 1H), 3.20 (s, 3H), 3.66 (s, 3H), 6.89–6.97 (m, 2H), 7.02–7.08 (m, 2H). MS (ESI) $(M+H)^+$ 224.20

Compound 4

A mixture of compound 3 (2.06 g, 10 mmol) and $LiAlH_4$ (418 mg, 11 mmol) in THF (60 mL) was stirred for 0.5 h at 0° C. After cooling to −30 C, the resulting mixture was quenched sequentially with water (0.4 mL, 10 N NaOH (0.4 mL), and water (0.8 mL). After filtration and concentration, the residue was extracted with $CH_2Cl_2$. The organic layer was washed with brine, dried over $MgSO_4$, and concentrated to give concentrated to give 4 (1.46 g, 99%) as an oil which was used in the next step without purification. $^1H$ NMR (300 MHz, $CDCl_3$) δ 1.46–1.58 (m, 1H), 1.76–1.86 (m, 1H), 2.23–2.30 (m, 1H), 2.54–2.63 (m, 1H), 7.00 (d, 2H, J=6 Hz), 8.50 (d, 2H, J=6.0 Hz), 9.41 (d, 1H, J=4.5 Hz).

Compound 4a

The title compound was prepared by the general procedure described in 4 using 3a (2.8 g, 12.5 mmol). Concentration gave 4a (2.06 g, 100%) as an oil. $^1H$ NMR (300 MHz, CDCl3): δ 1.41–1.48 (m, 1H), 1.53–1.59 (m, 1H), 1.96–2.02 (m, 1H), 2.72–2.82 (m, 1H), 6.92–7.24 (m, 4H), 9.34 (d, 1H, J=4.7 Hz).

Compound 4b

The title compound was prepared by the general procedure described in 4 using 3b (5.5 g, 24.6 mmol). Concentration gave 4b (4.05 g, 100%) as an oil. $^1H$ NMR (300 MHz, $CDCl_3$): δ 1.43–1.50 (m, 1H), 1.67–1.73 (m, 1H), 2.07–2.14 (m, 1H), 2.56–2.63 (m, 1H), 6.93–6.99 (m, 2H), 7.03–7.09 (m, 2H), 9.31 (d,1H, J=4.6 Hz).

Compound 5

A mixture of compound 4 (1.46 g, 10 mmol), NH$_2$O H.HCl (1.4 g, 20 mmol), and 5 N NaOH (4 mL) in THF (50 mL) was refluxed for 0.5 h. After cooling to −30° C., the resulting mixture was quenched sequentially with water (0.4 mL, 10 N NaOH (0.4 mL), and water (0.8 mL). After concentration, the residue was extracted with CH$_2$Cl$_2$. The organic layer was washed with brine, dried over MgSO$_4$, and concentrated to give concentrated to give 5 (1.6 g, 99%) as an oil which was used in the next step without purification. $^1$H NMR (300 MHz, CDCl$_3$) δ 1.34–1.46 (m, 1H), 1.82–1.99 (m, 1.7H), 2.10–2.16 (m, 1H), 2.65–2.72 (m, 0.3H), 6.23 (d, 0.3 H, J=8.4 Hz), 7.00 (m, 2H), 7.21 (d, 0.7H, J=7.3 Hz), 8.4(m, 2H).

Compound 5a

The title compound was prepared by the general procedure described in 5 using 4a (2.06 g, 12.5 mmol). Concentration gave 5a (2.03 g,90%) as an oil.

Compound 5b

The title compound was prepared by the general procedure described in 5 using 4b (4.05 g, 24.6 mmol). Concentration gave 5b (4.35 g, 98%) as an oil.

Compound 6

A mixture of compound 5 (1.58 g, 9.7 mmol) and LiAlH$_4$ (0.57 g, 15 mmol) in THF (60 mL) was refluxed for 1. After cooling to −30° C., the resulting mixture was quenched sequentially with water (0.6 mL), 10 N NaOH (0.6 mL), and water (1.2 mL). After concentration, the residue was extracted with CH$_2$Cl$_2$. The organic layer was washed with brine, dried over MgSO$_4$, and concentrated to give concentrated to give 6 (1.3 g, 91%) as an oil which was used in the next step without purification. LCMS (99%); LCMS (M+1)$^+$ 149.10.

Compound 6a

The title compound was prepared by the general procedure described in 6 using 5a (2.03 g, 11.3 mmol). Concentration gave 6a (1.75 g, 94%) as an oil. $^1$H NMR (300 MHz, CDCl$_3$): δ 0.80–1.00 (m, 2H), 1.87–2.00 (m, 2H), 2.22–2.82 (m, 2H), 6.86–7.24 (m, 4H).

Compound 6b

The title compound was prepared by the general procedure described in 6 using 5b (4.35 g, 24.3 mmol). Concentration gave 6b (3.39 g, 85%) as an oil. $^1$H NMR (300 MHz, CDCl$_3$): δ 0.78–0.89 (m, 2H), 1.15–1.22 (m, 1H), 168–1.88 (m, 1H), 2.69–2.87 (m, 1H), 6.80–7.10 (m, 4H).

Compound 7

(±)-trans-N-(1-Phenyl-ethyl)-N'-(2-pyridin-4-yl-cyclopropylmethyl)-[1,3,5]triazine-2,4,6-triamine A mixture of compound 6 (400 mg, 3 mmol), triazine (249 mg, 1 mmol), and N,N-diisopropyl ethylamine (2 mL) in THF (10 mL) was refluxed for 3 days. After concentration, purification on silica gel gave 7 (320 mg, 80%) as an oil. LCMS (100%); LCMS (M+1)$^+$ 362.88.

Compound 7a (±)-trans-N-[2-(2-Fluoro-phenyl)-cyclopropylmethyl]-N'-(1-phenyl-ethyl)-[1,3,5]triazine-2,4,6-triamine The title compound was prepared by the general procedure described in 7 using 6a (165 mg, 1 mmol). After concentration, purification on silica gel gave 7a (130 mg, 34%) as an oil. LCMS (99%); LCMS (M+1)$^+$ 379.22.

Compound 7b (±)-trans-N-[2-(4-Fluoro-phenyl)-cyclopropylmethyl]-N'-(1-phenyl-ethyl)-[1,3,5]triazine-2,4,6-triamine The title compound was prepared by the general procedure described in 7 using 6b (165 mg, 1 mmol). After concentration, purification on silica gel gave 7b (245 mg, 64%) as an oil. LCMS (98%); LCMS (M+1)$^+$ 379.22.

Compound 8a (S,S)-trans-N-[2-(2-Fluoro-phenyl)-cyclopropylmethyl]-N'-(1-phenyl-ethyl)-[1,3,5]triazine-2,4,6-triamine Diastereomers 7a (12 mg) was subjected to Chiralpak AD column separation with an eluant of 15% isopropanol/85% hexane to give 8a (6 mg, 50%) as an oil. LCMS (99%); LCMS (M+1)$^+$ 379.22.

Compound 8b (S,S)-trans-N-[2-(4-Fluoro-phenyl)-cyclopropyl methyl]-N'-(1-phenyl-ethyl)-[1,3,5]triazine-2,4,6-triamine Diastereomers 7b (20 mg) was subjected to Chiralpak AD column separation with an eluant of 15%isopropanol/85%hexane to give 8b (9.7 mg, 50%) as an oil. LCMS (99%); LCMS (M+1)$^+$ 379.22.

5-HT$_7$ Receptor Binding Assay

Membranes are prepared for binding using the human 5-HT$_7$ receptor expressed in CHO cells. Cells are collected and ruptured using a dounce homogenizer. The cells are spun at 18000× g for 10 minutes and the pellet is resuspended in assay buffer, frozen in liquid nitrogen and kept at −80° C. until the day of the assay.

A total of 30 ug protein is used per well. The assay is carried out in 96-deep-well plates. The assay buffer is 50 mM HEPES. The membrane preparation is incubated at 25° C. for 60 minutes with 0.1 nM to 1000 nM test compound and 1 nM $^3$H-5-carboxamidotryptamine. 10 uM serotonin is used as blocking agent to determine non-specific binding. The reaction is terminated by the addition of 1 ml of ice cold 50mM HEPES buffer and rapid filtration through a Brandel Cell Harvester using Whatman GF/B filters. The filter pads are counted in an LKB Trilux liquid scintillation counter. IC$_{50}$ values are determined using non-linear regression by Exel-fit.

Biological Activity

The compounds of this invention are useful as antagonists or partial agonists for the treatment of CNS and ocular disorders. The compounds of the present invention have been evaluated for 5-HT$_7$ receptor activity and have IC$_{50}$s of approximately 200 nM or less in the 5-HT$_7$ receptor binding assay. A compound of this invention has also been assessed in an in vivo model, the rat pup isolation-induced ultrasonic vocalization test. This animal model has proven to be a sensitive and reliable method for detecting anxiolytics and antidepressants across a broad spectrum of pharmacological classes such as benzodiazepines, serotonin reuptake inhibitors, serotonin agonists and NMDA antagonists (Gardner, C.; *Drug Devel. Res.* 1985, 5,185–193 and Winslow, J.; Insel, T.; *Psychopharmacology* 1991, 105, 513–520). Administration of N$^2$-[(1S)-1-(4-Methylphenyl) ethyl]-N$^4$-(2-phenoxyethyl)-1,3,5-triazine-2,4,6-triamine, produced a dose dependent and significant supression of rat pup ultrasonic vocalization at doses which did not suppress locomotor activity. The amount of compound dosed which reduced the rat pup ultrasonic vocalization by 50% (ID$_{50}$) was 23.8 mg/kg.

The following compounds were found to have an IC$_{50's}$ less than or equal to 50 nM in the 5-HT7 receptor assay:

N$^4$-[(1S)-1-(4-Bromophenyl)ethyl]-N$^2$-(2-phenoxyethyl) pyrimidine-2,4-diamine, Compound 13, N$^4$-(3-Methylphenylmethyl)-N$^2$-(2-phenoxyethyl) pyrimidine-2,4-diamine, N$^2$-(2-Phenoxyethyl)-N$^4$-[(1S)-1-phenylethyl] pyrimidine-2,4-diamine, N$^4$-{3-[(Methylsulfonyl)amino]phenylmethyl}-N$^2$-(2-phenoxyethyl)pyrimidine-2,4-diamine, Compound 14, $N^2$-(2-Phenoxyethyl)-$N^4$-[3-(trifluoromethyl) phenylmethyl]pyrimidine-2,4-diamine, $N^4$-(3-Chlorophenylmethyl)-$N^2$-(2-phenoxyethyl) pyrimidine-2,4-diamine, $N^2$-(2-Phenoxyethyl)-$N^4$-[(1S)-1-phenylpropyl] pyrimidine-2,4-diamine, $N^4$-(4-Chlorophenylmethyl)-$N^2$-(2-phenoxyethyl) pyrimidine-2,4-diamine, $N^4$-(3-Iodophenylmethyl)-$N^2$-(2-phenoxyethyl) pyrimidine-2,4-diamine, Compound 15, $N^4$-(3,4-Difluorophenylmethyl)-$N^2$-(2-phenoxyethyl) pyrimidine-2,4-diamine, $N^4$-(4-Benzodioxolylmethyl)-$N^2$-(2-phenoxyethyl) pyrimidine-2,4-diamine, $N^2$-(2-Phenoxyethyl)-$N^4$-(phenylmethyl)pyrimidine-2,4-diamine, $N^4$-(3-Methylphenyl methyl)-$N^2$-(2-phenoxyethyl) pyrimidine-2,4-diamine, $N^4$-(3-Chloro-4-methylphenylmethyl)-$N^2$-(2-phenoxyethyl)pyrimidine-2,4-diamine, $N^4$-[1-(4-Chlorophenyl)ethyl]-$N^2$-(2-phenoxyethyl) pyrimidine-2,4-diamine, $N^4$-(1-Napthalenylmethyl)-$N^2$-(2-phenoxyethyl) pyrimidine-2,4-diamine, Compound 16, $N^4$-[(1S)-1-(1-Napthalenyl)ethyl]-$N^2$-(2-phenoxyethyl) pyrimidine-2,4-diamine, Compound 17, $N^2$-(2-Phenoxyethyl)-$N^4$-(2-thienylmethyl)pyrimidine-2,4-diamine, Compound 18, $N^4$-[(1S)-1-(4-Methylphenyl)ethyl]-$N^2$-(2-phenoxyethyl) pyrimidine-2,4-diamine, $N^4$-[4-(1-Methylethyl)phenylmethyl]-$N^2$-(2-phenoxyethyl)pyrimidine-2,4-diamine, $N^4$-[2-Fluoro-5-(trifluoromethyl)phenylmethyl]-$N^2$-(2-phenoxyethyl)pyrimidine-2,4-diamine, $N^2$-(2-Phenoxyethyl)-N4-(4-pyridinylmethyl)pyrimidine-2,4-diamine, Compound 19, $N^4$-(3-Chloro-4-fluorophenylmethyl)-$N^2$-(2-phenoxyethyl)pyrimidine-2,4-diamine, $N^2$-(2-Phenoxyethyl)-$N^4$-(3-pyridinylmethyl)pyrimidine-2,4-diamine, Compound 20, $N^2$-[2-(3-Hydroxyphenyl)ethyl]-$N^4$-(1-phenylethyl) pyrimidine-2,4-diamine, Compound 21, $N^4$-[(1S)-1-Phenylethyl]-$N^2$-(2-phenylethyl)pyrimidine-2,4-diamine, $N^2$-(2-Phenylethyl)-$N^4$-[(1S)-1-phenylpropyl] pyrimidine-2,4-diamine, $N^2$-[2-(4-Hydroxyphenyl)ethyl]-$N^4$-(1-phenylethyl) pyrimidine-2,4-diamine, $N^2$-[2-(3-Fluorophenyl)ethyl]-$N^4$-(1-phenylethyl) pyrimidine-2,4-diamine, $N^4$-[1-(4-Fluorophenyl)ethyl]-$N^2$-(2-phenylethyl) pyrimidine-2,4-diamine, $N^2$-[2-(2-Fluorophenyl)ethyl]-$N^4$-(1-phenylethyl) pyrimidine-2,4-diamine, $N^4$-(2-Methoxyphenylmethyl)-$N^2$-(2-phenylethyl) pyrimidine-2,4-diamine, $N^2$-[2-(3-Methoxyphenyl)ethyl]-$N^4$-(1-phenylethyl) pyrimidine-2,4-diamine, $N^2$-[2-(3-Fluorophenyl)ethyl]-$N^4$-(1-phenylethyl) pyrimidine-2,4-diamine, $N^2$-[2-(4-Fluorophenyl)ethyl]-$N^4$-(1-phenylethyl) pyrimidine-2,4-diamine, $N^2$-[2-(3-Cyanophenyl)ethyl]-$N^4$-(1-phenylethyl) pyrimidine-2,4-diamine, Compound 22, $N^2$-[2-(1-Cyclohexenyl)ethyl]-$N^4$-(1-phenylethyl) pyrimidine-2,4-diamine, Compound 23, $N^2$-[2-(3-Chlorophenyl)ethyl]-$N^4$-(1-phenylethyl) pyrimidine-2,4-diamine, $N^4$-[(1S)-1-(1-Napthalenyl)ethyl]-$N^2$-(2-phenylethyl) pyrimidine-2,4-diamine, Compound 24, $N^4$-(1-Methyl-1-phenyl)ethyl)-$N^2$-(2-phenylethyl) pyrimidine-2,4-diamine, $N^4$-(3-Iodophenylmethyl)-$N^2$-(2-phenylethyl)pyrimidine-2,4-diamine, Compound 25, $N^2$-(2-Phenylethyl)-$N^4$-(phenylmethyl)pyrimidine-2,4-diamine, $N^4$-(3-Methylphenylmethyl)-$N^2$-(2-phenylethyl) pyrimidine-2,4-diamine, $N^4$-(4-Chlorophenylmethyl)-$N^2$-(2-phenylethyl) pyrimidine-2,4-diamine, $N^4$-(3-Bromophenylmethyl)-$N^2$-(2-phenylethyl) pyrimidine-2,4-diamine, Compound 26, $N^4$-(3-Fluorophenylmethyl)-$N^2$-(2-phenylethyl) pyrimidine-2,4-diamine, $N^2$-(2-Phenylethyl)-$N^4$-(2-thienylmethyl)pyrimidine-2,4-diamine, Compound 27, $N^4$-[1-(4-Chlorophenyl)ethyl]-$N^2$-(2-phenylethyl) pyrimidine-2,4-diamine, $N^2$-[2-(4-Methylphenyl)ethyl]-$N^4$-(1-phenylethyl) pyrimidine-2,4-diamine, $N^2$-(Methyl)-$N^2$-(2-phenylethyl)-$N^4$-(1-phenylethyl) pyrimidine-2,4-diamine, $N^4$-(3,4-Difluorophenylmethyl)-$N^2$-(2-phenylethyl) pyrimidine-2,4-diamine, $N^4$-(4-Benzodioxolylmethyl)-$N^2$-(2-phenylethyl) pyrimidine-2,4-diamine, $N^4$-(2-Chlorophenylmethyl)-$N^2$-(2-phenylethyl) pyrimidine-2,4-diamine, $N^4$-(3-Chloro-4-fluorophenylmethyl)-$N^2$-(2-phenylethyl) pyrimidine-2,4-diamine, $N^4$-(3-Methoxyphenylmethyl)-$N^2$-(2-phenylethyl) pyrimidine-2,4-diamine, $N^4$-(4-Methoxyphenylmethyl)-$N^2$-(2-phenylethyl) pyrimidine-2,4-diamine, $N^2$-(2-Phenylethyl)-$N^4$-[3-(trifluoromethyl) phenylmethyl]pyrimidine-2,4-diamine, $N^2$-[2-(1H-Indol-1-yl)ethyl]-$N^4$-(1-phenylethyl) pyrimidine-2,4-diamine, Compound 28, $N^4$-(1-Phenylethyl)-$N^2$-[2-(2-thienyl)ethyl]pyrimidine-2,4-diamine, Compound 29, $N^2$-[2(1H-Indol-3-yl)ethyl]-$N^2$-(methyl)-$N^4$-(1-phenylethyl)pyrimidine-2,4-diamine, Compound 30, $N^2$-[2-(6-Fluoro-1H-indol-3-yl)ethyl]-$N^4$-(1-phenylethyl) pyrimidine-2,4-diamine, Compound 31, $N^4$-[2-(4-Fluorophenoxy)ethyl]-$N^2$-(1-phenylethyl) pyrimidine-2,4-diamine, $N^4$-[2-(4-Hydroxyphenyl)ethyl]-$N^6$-[(1S)-1-phenylethyl] pyrimidine-4,6-diamine, $N^4$-[2-(4-Fluorophenoxy)ethyl]-$N^6$-[(1S)-1-phenylethyl] pyrimidine-4,6-diamine, Example 16, $N^2$-[(1S)-1-Phenylethyl]-$N^4$-(2-phenylethyl)-1,3,5-triazine-2,4,6-triamine, Compound 60, $N^2$-[2-(3-Fluorophenyl)ethyl]-$N^4$-[(1S)-1-phenylethyl]-1,3,5-triazine-2,4,6-triamine, Compound 61, $N^2$-[2-(3-Chlorophenyl)ethyl]-$N^4$-[(1S)-1-phenylethyl]-1,3,5-triazine-2,4,6-triamine, Compound 62, $N^2$-[2-(3-Fluorophenyl)ethyl]-$N^4$-[(1S)-1-phenylpropyl]-1,3,5-triazine-2,4,6-triamine, Compound 63, $N^2$-[2-(4-Fluorophenyl)ethyl]-$N^4$-[(1S)-1-phenylethyl]-1,3,5-triazine-2,4,6-triamine, Compound 64, $N^2$-2-Phenylethyl-$N^4$-[(1S)-1-phenylpropyl]-1,3,5-triazine-2,4,6-triamine, Compound 65, $N^2$-[2-(3-Bromophenyl)ethyl]-$N^4$-[(1S)-1-phenylethyl]-1,3,5-triazine-2,4,6-triamine, Compound 66, $N^2$-[2-(4-Fluorophenyl)ethyl]-$N^4$-[(1S)-1-phenylpropyl]-1,3,5-triazine-2,4,6-triamine, Compound 67, $N^2$-[(1S)-1-(4-Bromophenyl)ethyl]-$N^4$-[2-(3-fluorophenyl)ethyl]-1,3,5-triazine-2,4,6-triamine, Compound 68, $N^2$-[2-(3-Chlorophenyl)ethyl]-$N^4$-[(1S)-1-phenylpropyl]-1,3,5-triazine-2,4,6-triamine, Compound 69, $N^2$-[(1S)-1-(4-Bromophenyl)ethyl]-$N^4$-[2-(4-fluorophenyl)ethyl]-1,3,5-triazine-2,4,6-triamine, Compound 70, $N^2$-[2-(3,4-Dichlorophenyl)ethyl]-$N^4$-[(1S)-1-phenylethyl]-1,3,5-triazine-2,4,6-triamine, Compound 71, $N^2$-[2-(4-Methylphenyl)ethyl]-$N^4$-[(1S)-1-phenylethyl]-1,3,5-triazine-2,4,6-triamine, Compound 72, $N^2$-[2-(3-Hydroxyphenyl)ethyl]-$N^4$-[(1S)-1-phenylethyl]-1,3,5-triazine-2,4,6-triamine, Compound 73, $N^2$-[2-(4-Fluorophenyl)ethyl]-$N^4$-[(1S)-1-(4-nitrophenyl)ethyl]-1,3,5-triazine-2,4,6-triamine, Compound 74, $N^2$-[2-(4-Hydroxyphenyl)ethyl]-$N^4$-[(1S)-1-(4-nitrophenyl)ethyl]-1,3,5-triazine-2,4,6-triamine, Compound 75, $N^2$-[2-(2-Fluorophenyl)ethyl]-$N^4$-[(1S)-1-(4-nitrophenyl)ethyl]-1,3,5-triazine-2,4,6-triamine, Compound 76, $N^2$-[2-(3-Methoxyphenyl)ethyl]-$N^4$-[(1S)-1-(4-nitrophenyl)ethyl]-1,3,5-triazine-2,4,6-triamine, Compound 77, $N^2$-[2-(4-Aminophenyl)ethyl]-$N^4$-[(1S)-1-(4-nitrophenyl)ethyl]-1,3,5-triazine-2,4,6-triamine, Compound 78, $N^2$-[2-(4-Methylphenyl)ethyl]-$N^4$-[(1S)-1-(4-nitrophenyl)ethyl]-1,3,5-triazine-2,4,6-triamine, Compound 79, $N^2$-[2-(4-Hydroxy-3-methoxyphenyl)ethyl]-$N^4$-[(1S)-1-(4-nitrophenyl)ethyl]--1,3,5-triazine-2,4,6-triamine, Compound 80, $N^2$-[(1S)-1-(4-Fluorophenyl)ethyl]-$N^4$-[2-(4-fluorophenyl)ethyl]-1,3,5-triazine-2,4,6-triamine, Example 17, $N^2$-[(1S)-1-(4-Fluorophenyl)ethyl]-$N^4$-[2-(2-pyridinyl)ethyl]-1,3,5-triazine-2,4,6-triamine, Example 18, 21, $N^2$-[(1S)-1-(4-Fluorophenyl)ethyl]-$N^4$-[2-(2-pyridinyl)ethyl]-1,3,5-triazine-2,4,6-triamine, Examples 18, 21, and $N^2$-(2-Chlorophenylmethyl)-$N^4$-(2-phenylethyl)-1,3,5-triazine-2,4,6-triamine, $N^2$-[2-(3-Fluorophenyl)ethyl]-6-methyl-$N^4$-[(1S)-1-phenylethyl]pyrimidine-2,4-diamine, $N^2$-[2-(3-Methoxyphenyl)ethyl]-6-methyl-$N^4$-[(1S)-1-phenylethyl]pyrimidine-2,4-diamine, $N^2$-[2-(3-Bromophenyl)ethyl]-6-methyl-$N^4$-[(1S)-1-phenylethyl]pyrimidine-2,4-diamine, $N^2$-[2-(3-Cyanophenyl)ethyl]-6-methyl-$N^4$-[(1S)-1-phenylethyl]pyrimidine-2,4-diamine, $N^2$-[2-(4-Chlorophenyl)ethyl]-6-methyl-$N^4$-[(1S)-1-phenylethyl]pyrimidine-2,4-diamine, and $N^2$-[2-(4-Methylphenyl)ethyl]-6-methyl-$N^4$-[(1S)-1-phenylethyl]pyrimidine-2,4-diamine.

$N^2$-[2-(2-Methoxyphenyl)ethyl]-6-methyl-$N^4$-[(1S)-1-phenylethyl]pyrimidine-2,4-diamine, (S,S)-trans-N-[2-(4-Fluoro-phenyl)-cyclopropylmethyl]-N'-(1-phenyl-ethyl)-[1,3,5]triazine-2,4,6-triamine, (S,S)-trans-N-[2-(2-Fluoro-phenyl)-cyclopropylmethyl]-N'-(1-phenyl-ethyl)-[1,3,5]triazine-2,4,6-triamine, and (±)-trans-N-(1-Phenyl-ethyl)-N'-(2-pyridin-4-yl-cyclopropylmethyl)-[1,3,5]triazine-2,4,6-triamine. The following compounds were found to have an IC$_{50}$ within the range of 51–100 nM in the 5-HT7 receptor assay:

$N^4$-(3-Fluorophenylmethyl)-$N^2$-(2-phenoxyethyl)pyrimidine-2,4-diamine, $N^4$-[4-Fluoro-3-(trifluoromethyl)phenylmethyl]-$N^2$-(2-phenoxyethyl)pyrimidine-2,4-diamine, $N^4$-[3-(Aminocarbonyl)phenylmethyl]-$N^2$-(2-phenoxyethyl)pyrimidine-2,4-diamine, Compound 6, $N^4$-[(1R)-1-(4-Methylphenyl)ethyl]-$N^2$-(2-phenoxyethyl)pyrimidine-2,4-diamine, $N^4$-(1-Phenylethyl)-$N^2$-(2-phenylpropyl)pyrimidine-2,4-diamine, $N^4$-(1-Phenylethyl)-$N^2$-(3-phenylpropyl)pyrimidine-2,4-diamine, $N^2$-(2-Phenthioethyl)-$N^4$-(1-phenylethyl)pyrimidine-2,4-diamine, $N^2$-[2-(4-Chlorophenyl)ethyl]-$N^4$-(1-phenylethyl)pyrimidine-2,4-diamine, $N^4$-[2-(1H-Indol-3-yl)ethyl]-$N^2$-(1-phenylethyl)pyrimidine-2,4-diamine, Compound 7, $N^2$-(2-Phenylethyl)-$N^4$-[(1R)-1-phenylpropyl]pyrimidine-2,4-diamine, $N^2$-[2-(3-Bromophenyl)ethyl]-$N^4$-(1-phenylethyl)pyrimidine-2,4-diamine, Compound 8, $N^2$-[2-(4-Bromophenyl)ethyl]-$N^4$-(1-phenylethyl)pyrimidine-2,4-diamine, Compound 9, $N^4$-(2,4-Dichlorophenylmethyl)-$N^2$-(2-phenylethyl)pyrimidine-2,4-diamine, $N^2$-[2-(3,4-Dichlorophenyl)ethyl]-$N^4$-(1-phenylethyl)pyrimidine-2,4-diamine, $N^2$-(Indan-2-yl)-N4-(1-phenylethyl)pyrimidine-2,4-diamine, Compound 10, $N^2$-(2-Phenylethyl)-$N^4$-(3-pyridinylmethyl)pyrimidine-2,4-diamine, Compound 11, $N^4$-(1-Phenylethyl)-$N^2$-{2-[3-(trifluoromethyl)phenyl]ethyl}pyrimidine-2,4-diamine, $N^2$-[2-(2-Methoxyphenyl)ethyl]-$N^4$-(1-phenylethyl)pyrimidine-2,4-diamine, $N^4$-(1-Phenylethyl)-$N^2$-[2-(2-pyridinyl)ethyl]pyrimidine-2,4-diamine, Compound 12, $N^2$-[2-(Phenoxy)ethyl]-$N^4$-[(1S)-1-phenylpropyl]-1,3,5-triazine-2,4,6-triamine, Compound 40, $N^2$-[2-(Phenoxy)ethyl]-$N^4$-[(1S)-1-phenylethyl]-1,3,5-triazine-2,4,6-triamine, Compound 41, Examples 19, 20, $N^2$-[(1S)-1-(1-Napthyl)ethyl]-$N^4$-[2-(phenoxy)ethyl]-1,3,5-triazine-2,4,6-triamine, Compound 42, N²-[2-(4-Fluorophenoxy)ethyl]-N⁴-[1-(4-fluorophenyl)ethyl]-1,3,5-triazine-2,4,6-triamine, Compound 43, N²-[2-(4-Fluorophenoxy)ethyl]-N⁴-[(1S)-1-(4-fluorophenyl)ethyl]-1,3,5-triazine-2,4,6-triamine, Compound 44, N²-[2-(4-Fluorophenoxy)ethyl]-N⁴-[(1S)-1-(4-nitrophenyl)ethyl]-1,3,5-triazine-2,4,6-triamine, Compound 45, N²-[2-(4-Fluorophenoxy)ethyl]-N⁴-[(1R)-1-(4-fluorophenyl)ethyl]-1,3,5-triazine-2,4,6-triamine, Compound 46, N²-[2-(3,4-Difluorophenoxy)ethyl]-N⁴-[(1S)-1-(4-nitrophenyl)ethyl]-1,3,5-triazine-2,4,6-triamine, Compound 47, N²-[2-(2-Fluorophenyl)ethyl]-N⁴-[(1S)-1-phenylethyl]-1,3,5-triazine-2,4,6-triamine, Compound 48, N²-[2-(4-Methylphenyl)ethyl]-N⁴-[(1S)-1-phenylpropyl]-1,3,5-triazine-2,4,6-triamine, Compound 49, N²-[2-(4-Chlorophenyl)ethyl]-N⁴-[(1S)-1-phenylethyl]-1,3,5-triazine-2,4,6-triamine, Compound 50, N²-[2-(2-Fluorophenyl)ethyl]-N⁴-[(1S)-1-phenylpropyl]-1,3,5-triazine-2,4,6-triamine, Compound 51, N²-[2-(3-Methoxyphenyl)ethyl]-N⁴-[(1S)-1-phenylpropyl]-1,3,5-triazine-2,4,6-triamine, Compound 52, N²-[(1S)-1-Phenylethyl]-N⁴-{2-[3-(trifluoromethyl)phenyl]ethyl}-1,3,5-triazine-2,4,6-triamine, Compound 53, N²-[2-(3-Methoxyphenyl)ethyl]-N⁴-[(1S)-1-phenylethyl]-1,3,5-triazine-2,4,6-triamine, Compound 54, N²-[2-(3-Cyanophenyl)ethyl]-N⁴-[(1S)-1-phenylethyl]-1,3,5-triazine-2,4,6-triamine, Compound 55, N²-[(1S)-1-(1-Napthalenyl)ethyl]-N⁴-(2-phenylethyl)-1,3,5-triazine-2,4,6-triamine, Compound 56, N²-[2-(1-Cyclohexenyl)ethyl]-N⁴-[(1S)-1-phenylethyl]-1,3,5-triazine-2,4,6-triamine, Compound 57

N²-[2-(3-Chlorophenyl)ethyl]-N⁴-[(1S)-1-(4-nitrophenyl)ethyl]-1,3,5-triazine-2,4,6-triamine, Compound 58 and N²-[2-(4-Chlorophenyl)ethyl]-N⁴-[(1S)-1-(4-nitrophenyl)ethyl]-1,3,5-triazine-2,4,6-triamine, Compound 59.

N²-[2-(3,5-Dimethoxyphenyl)ethyl]-6-methyl-N⁴-[(1S)-1-phenylethyl]pyrimidine-2,4-diamine, and N²-[2-(3-Bromo-4-methoxyphenyl)ethyl]-6-methyl-N⁴-[(1S)-1-phenylethyl]pyrimidine-2,4-diamine.

The following compounds were found to have an IC₅₀ within the range of 101–200 nM in the 5-HT7 receptor assay:

N⁴-(3,4-Dichlorophenylmethyl)-N²-(2-phenoxyethyl)pyrimidine-2,4-diamine,

N²-(2-Phenoxyethyl)-N⁴-[(1R)-1-phenylpropyl]pyrimidine-2,4-diamine,

N²-(2-Phenoxyethyl)-N⁴-[4-(trifluoromethyl)phenylmethyl]pyrimidine-2,4-diamine,

N⁴-(3,5-Difluorophenylmethyl)-N²-(2-phenoxyethyl)pyrimidine-2,4-diamine,

N²-(2-Phenoxyethyl)-N⁴-[(1R)-1-phenylethyl]pyrimidine-2,4-diamine,

N⁴-[3-Fluoro-5-(trifluoromethyl)phenylmethyl]-N²-(2-phenoxyethyl)pyrimidine-2,4-diamine, N⁴-(3,5-Dimethoxyphenylmethyl)-N²-(2-phenoxyethyl)pyrimidine-2,4-diamine, N⁴-(1-Phenylethyl)-N²-[2-(3-pyridinyl)ethyl]pyrimidine-2,4-diamine, Compound 1, N⁴-(3,4-Dichlorophenylmethyl)-N²-(2-phenylethyl)pyrimidine-2,4-diamine, N⁴-(2-Furanylmethyl)-N²-(2-phenylethyl)pyrimidine-2,4-diamine, Compound 2

N⁴-(3-Chloro-4-methylphenylmethyl)-N²-(2-phenylethyl)pyrimidine-2,4-diamine,

N²-[2-(4-Methoxyphenyl)ethyl]-N⁴-(1-phenylethyl)pyrimidine-2,4-diamine,

N⁴-(3-Chlorophenylmethyl)-N²-(2-phenylethyl)pyrimidine-2,4-diamine,

N²-(2-Phenylethyl)-N⁴-[(1R)-1-phenylethyl]pyrimidine-2,4-diamine,

N²-(2-Phenylethyl)-N⁴-[4-(trifluoromethyl)phenylmethyl]pyrimidine-2,4-diamine,

N⁴-[4-Fluoro-3-(trifluoromethyl)phenylmethyl]-N²-(2-phenylethyl)pyrimidine-2,4-diamine, N²-[2-(4-Benzodioxolyl)ethyl]-N⁴-(1-phenylethyl)pyrimidine-2,4-diamine and N²-[2-(5-Fluoro-1H-indol-3-yl)]ethyl]-N⁴-(1-phenylethyl)pyrimidine-2,4-diamine, Compound 3, N⁴-(2-Furanylmethyl)-N²-(2-phenoxyethyl)pyrimidine-2,4-diamine, Compound 4, and N²-(2-Phenylethyl)-N⁴-(4-pyridinylmethyl)pyrimidine-2,4-diamine, N⁴-[2-(4-Aminophenyl)ethyl]-N⁶-[(1S)-1-phenylethyl]pyrimidine-4,6-diamine, N⁴-[2-(4-Bromoophenyl)ethyl]-N⁶-[(1S)-1-phenylethyl]pyrimidine-4,6-diamine, N²-[2-(4-Chlorophenyl)ethyl]-N⁴-[(1S)-1-phenylpropyl]-1,3,5-triazine-2,4,6-triamine, Compound 32, N²-[2-(3,4-Dichlorophenyl)ethyl]-N⁴-[(1S)-1-phenylpropyl]--1,3,5-triazine-2,4,6-triamine, Compound 33, N²-[(1S)-1-(4-Bromophenyl)ethyl]-N⁴-[2-(4-methylphenyl)ethyl]-1,3,5-triazine-2,4,6-triamine, Compound 34, N²-[(1S)-1-Phenylpropyl]-N⁴-(2-phenylpropyl)-1,3,5-triazine-2,4,6-triamine, Compound 35, N²-[(1S)-1-Phenylpropyl]-N⁴-[2-(3-(trifluoromethyl)phenyl)ethyl]-1,3,5-triazine-2,4,6-triamine, Compound 36, N²-[(1S)-1-Phenylethyl]-N⁴-(2-phenylpropyl)-1,3,5-triazine-2,4,6-triamine, Compound 37, N²-[(1S)-1-(1-Napthalenyl)ethyl]-N⁴-[2-(phenylamino)ethyl]-1,3,5-triazine-2,4,6-triamine, Compound 38, N²-[2-(4-Bromophenyl)ethyl]-N⁴-[(1S)-1-(4-nitrophenyl)ethyl]-1,3,5-triazine-2,4,6-triamine, Compound 39, N²-[2-(4-Methoxyphenyl)ethyl]-6-methyl-N⁴-[(1S)-1-phenylethyl]pyrimidine-2,4-diamine, and N²-[2-(3-Acetamidophenyl)ethyl]-6-methyl-N⁴-[(1S)-1-phenylethyl]pyrimidine-2,4-diamine.

The following compounds were found to have an IC50's less than or equal to 100 nM but greater than 50 nM in the 5-HT7 receptor assay:

(±)-trans-N-[2-(2-Fluoro-phenyl)-cyclopropylmethyl]-N'-(1-phenyl-ethyl)-[1,3,5]triazine-2,4,6-triamine, (S,S)-trans-N-[2-(4-Fluoro-phenyl)-cyclopropylmethyl]-N'-[1-(4-fluoro)phenyl-ethyl]-[1,3,5]triazine-2,4,6-triamine, and (±)-trans-N-[2-(4-Fluoro-phenyl)-cyclopropylmethyl]-N'-(1-phenyl-ethyl)-[1,3,5]triazine-2,4,6-triamine.

Compounds of Formula (Ia) may be useful as inhibitors of methyltransferase proteins. See Stephen W. Fesik et. al. "Novel Inhibitors of Erm Methyltransferases from NMR and Parallel Synthesis" J. Med. Chem. 1999, 42, 3852–3859.

What is claimed is:

1. A method of treating sleeping disorders, depression, hypertension, schizophrenia, anxiety, obsessive compulsive disorders and migraine comprising administration to a subject in need thereof an effective amount of a compound of Formula (I)

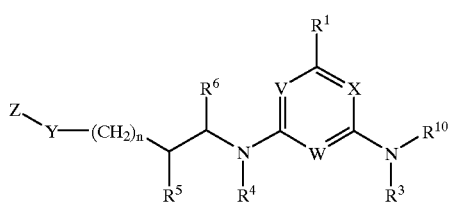

or a pharmaceutically acceptable salt or hydrate thereof, wherein

V, W and X are each N;

Y is O, $S(O)_m$, $CH_2$, $NR^9$ or a covalent bond;

Z is selected from the group consisting of benzodioxolyl, cyclohexenyl, furanyl, indolyl, napthalenyl, thienyl, pyridinyl and phenyl;
  optionally substituted with one to five groups, the same or different independently selected from the group consisting of halogen, $C_{1-4}$alkyl, $C_{1-4}$haloalkyl, $O-C_{1-4}$alkyl, cyano, hydroxy, nitro, $NHSO_2C_{1-6}$alkyl, $NR^7R^8$, $C(O)NH_2$ and $C_{1-3}$alkylene;

m and n are each independently 0, 1 or 2;

$R^1$ is halogen, $C_{1-6}$alkyl, $C_{3-7}$cycloalkyl or $NR^7R^8$;

$R^2$ is $C_{1-4}$alkyl substituted with Z', wherein
  Z' is selected from the group consisting of benzodioxolyl, cyclohexenyl, furanyl, indolyl, napthalenyl, thienyl, pyridinyl and phenyl;
    optionally substituted with one to five groups, the same or different independently selected from the group consisting of halogen, $C_{1-4}$alkyl, $C_{1-4}$haloalkyl, $O-C_{1-4}$alkyl, cyano, hydroxy, nitro, $NHSO_2C_{1-6}$alkyl, $NR^7R^8$ and $C(O)NH_2$;

$R^3$ is hydrogen, $C_{1-6}$alkyl or $C_{3-7}$cycloalkyl;

$R^4$ and $R^5$ are independently hydrogen or $C_{1-6}$alkyl or together are $C_{2-3}$alkylene;

$R^6$ is hydrogen or $C_{1-3}$alk(en)ylene provided that
  if $R^6$ is $C_{1-3}$alk(en)ylene, it is attached to Z;

$R^7$ and $R^8$ are independently selected from the group consisting of hydrogen, $C_{1-6}$alkyl, $C_{3-7}$cycloalkyl, $SO_2 C_{1-6}$alkyl;
  or $R^7$ and $R^8$ together with the nitrogen to which they are attached can form a 5 to 8 membered heterocycle;
    said heterocycle optionally containing a second heteroatom selected from the group consisting of N, O and S;
    said heterocycle being optionally substituted with up to three of the same or different substituents independently selected from $C_{1-6}$alkyl or $O-C_{1-6}$alkyl; and $R^9$ is hydrogen or $(C_{1-6})$alkyl.

2. The method according to claim 1 wherein $R^1$ is $NH_2$.

3. The method according to claim 1 wherein $R^1$ is $NH_2$ and Y is O.

4. The method according to claim 1 comprising administration to a subject in need thereof an effective amount of a compound (or a pharmaceutically acceptable salt or hydrate thereof), selected from the group consisting of $N^2$-[2-(4-Chlorophenyl)ethyl]-$N^4$-[(1S)-1-phenylpropyl]-1,3,5-triazine-2,4,6-triamine, $N^2$-[2-(3,4-Dichlorophenyl)ethyl]-$N^4$-[(1S)-1-phenylpropyl]-1,3,5-triazine-2,4,6-triamine, $N^2$-[(1S)-1-(4-Bromophenyl)ethyl]-$N^4$-[2-(4-methylphenyl)ethyl]-1,3,5-triazine-2,4,6-triamine, $N^2$-[(1S)-1-Phenylpropyl]-$N^4$-(2-phenylpropyl-1,3,5-triazine-2,4,6-triamine, $N^2$-[(1S)-1-Phenylpropyl]-$N^4$-[2-(3-(trifluoromethyl)phenyl)ethyl]-1,3,5-triazine-2,4,6-triamine, $N^2$-[(1S)-1-Phenylethyl]-$N^4$-(2-phenylpropyl)-1,3,5-triazine-2,4,6-triamine, $N^2$-[(1S)-1-(1-Napthalenyl)ethyl]-$N^4$-[2(phenylamino)ethyl]-1,3,5-triazine-2, 4,6-triamine, and $N^2$-[2-(4-Bromophenyl)ethyl]-$N^4$-[(1S)-1-(4-nitrophenyl)ethyl]-1,3,5-triazine-2,4,6-triamine.

5. The method according to claim 1 comprising administration to a subject in need thereof an effective amount of a compound (or a pharmaceutically acceptable salt or hydrate thereof), selected from the group consisting of $N^2$-[2-(Phenoxy)ethyl]-$N^4$-[(1S)-1-phenylpropyl]-1,3,5-triazine-2,4,6-triamine, $N^2$-[2-(Phenoxy)ethyl]-$N^4$-[(1S)-1-phenylethyl]-1,3,5-triazine-2,4,6-triamine, $N^2$-[(1S)-1-(1-Napthyl)ethyl]-$N^4$-[2-(phenoxy)ethyl]-1,3,5-triazine-2,4,6-triamine, $N^2$-[2-(4-Fluorophenoxy)ethyl]-$N^4$-[1-(4-fluorophenyl)ethyl]-1,3,5-triazine-2,4,6-triamine, $N^2$-[2-(4-Fluorophenoxy)ethyl]-$N^4$-[(1S)-1-(4-fluorophenyl)ethyl]-1,3,5-triazine-2,4,6-triamine, $N^2$-[2-(4-Fluorophenoxy)ethyl]-$N^4$-[(1S)-1-(4-nitrophenyl)ethyl]-1,3,5-triazine-2,4,6-triamine, $N^2$-[2-(4-Fluorophenoxy)ethyl]-$N^4$-[(1R)-1-(4-fluorophenyl)ethyl]-1,3,5-triazine-2,4,6-triamine, $N^2$-[2-(3,4-Difluorophenoxy)ethyl]-$N^4$-[(1S)-1-(4-nitrophenyl)ethyl]-1,3,5-triazine-2,4,6-triamine, $N^2$-[2-(2-Fluorophenyl)ethyl]-$N^4$-(1S)-1-phenylethyl]-1,3,5-triazine-2,4,6-triamine, $N^2$-[2-(4-Methylphenyl)ethyl]-$N^4$-[(1S)-1-phenylpropyl]-1,3,5-triazine-2,4,6-triamine, $N^2$-[2-(4-Chlorophenyl)ethyl]-$N^4$-[(1S)-1-phenylethyl]-1,3,5-triazine-2,4,6-triamine, $N^2$-[2-(2-Fluorophenyl)ethyl]-$N^4$-[(1S)-1-phenylpropyl]-1,3,5-triazine-2,4,6-triamine, $N^2$-[2-(3-Methoxylphenyl)ethyl]-$N^4$-[(1S)-1-phenylpropyl]-1,3,5-triazine-2,4,6-triamine, $N^2$-[(1S)-1-Phenylethyl]-$N^4$-{2-[3-(trifluoromethyl)phenyl]ethyl}-1,3,5-triazine-2,4,6-triamine, $N^2$-[2-(3-Methoxyphenyl)ethyl]-$N^4$-[(1S)-1-phenylethyl]-1,3,5-triazine-2,4,6-triamine, $N^2$-[2-(3-Cyanophenyl)ethyl]-$N^4$-[(1S)-1-phenylethyl]-1,3,5-triazine-2,4,6-triamine, $N^2$-[(1S)-1-(1-Napthalenyl)ethyl]-$N^4$-(2-phenylethyl)-1,3,5-triazine-2,4,6-triamine, $N^2$-[2-(1-Cyclohexenyl)ethyl]-$N^4$-[(1S)-1-phenylethyl]-1,3,5-triazine-2,4,6-triamine, N²-[2-(3-Chlorophenyl)ethyl]-N⁴-[(1S)-1-(4-nitrophenyl)ethyl]-1,3,5-triazine-2,4,6-triamine, and N²-[2-(4-Chlorophenyl)ethyl]-N⁴-[(1S)-1-(4-nitrophenyl)ethyl]-1,3,5-triazine-2,4,6-triamine.

6. The method according to claim 1 comprising administration to a subject in need thereof an effective amount of a compound (or a pharmaceutically acceptable salt or hydrate thereof), selected from the group consisting of N²-[(1S)-1-Phenylethyl]-N⁴-(2-phenylethyl)-1,3,5-triazine-2,4,6-triamine, N²-[2-(3-Fluorophenyl)ethyl]-N⁴-[(1S)-1-phenylethyl]-1,3,5-triazine-2,4,6-triamine, N²-[2-(3-Chlorophenyl)ethyl]-N⁴-[(1S)-1-phenylethyl]-1,3,5-triazine-2,4,6-triamine, N²-[2-(3-Fluorophenyl)ethyl]-N⁴-[(1S)-1-phenylpropyl]-1,3,5-triazine-2,4,6-triamine, N²-[2-(4-Fluorophenyl)ethyl]-N⁴-[(1S)-1-phenylethyl]-1,3,5-triazine-2,4,6-triamine, N²-2-Phenylethyl-N⁴-[(1S)-1-phenylpropyl]-1,3,5-triazine-2,4,6-triamine, N²-[2-(3-Bromophenyl)ethyl]-N⁴-[(1S)-1-phenylethyl]-1,3,5-triazine-2,4,6-triamine, N²-[2-(4-Fluorophenyl)ethyl]-N⁴-[(1S)-1-phenylpropyl]-1,3,5-triazine-2,4,6-triamine, N²-[(1S)-1-(4-Bromophenyl)ethyl]-N⁴-[2-(3-fluorophenyl)ethyl]-1,3,5-triazine-2,4,6-triamine, N²-[2-(3-Chlorophenyl)ethyl]-N⁴-[(1S)-1-phenylpropyl]-1,3,5-triazine-2,4,6-triamine, N²-[(1S)-1-(4-Bromophenyl)ethyl]-N⁴-[2-(4-fluorophenyl)ethyl]-1,3,5-triazine-2,4,6-triamine, N²-[2-(3,4-Dichlorophenyl)ethyl]-N⁴-[(1S)-1-phenylethyl]-1,3,5-triazine-2,4,6-triamine, N²-[2-(4-Methylphenyl)ethyl]-N⁴-[(1S)-1-phenylethyl]-1,3,5-triazine-2,4,6-triamine, N²-[2-(3-Hydroxyphenyl)ethyl]-N⁴-[-(1S)-1-phenylethyl]-1,3,5-triazine-2,4,6-triamine, N²-[2-(4-Fluorophenyl)ethyl]-N⁴-[(1S)-1-(4-nitrophenyl)ethyl]-1,3,5-triazine-2,4,6-triamine, N²-[2-(4-Hydroxyphenyl)ethyl]-N⁴-[-(1S)-1-(4-nitrophenyl)ethyl]-1,3,5-triazine-2,4,6-triamine, N²-[2-(2-Fluorophenyl)ethyl]-N⁴-[(1S)-1-(4-nitrophenyl)ethyl]-1,3,5-triazine-2,4,6-triamine, N²-[2-(3-Methoxyphenyl)ethyl]-N⁴-[(1S)-1-(4-nitrophenyl)ethyl]-1,3,5-triazine-2,4,6-triamine, N²-[2-(4-Aminophenyl)ethyl]-N⁴-[(1S)-1-(4-nitrophenyl)ethyl]-1,3,5-triazine-2,4,6-triamine, N²-[2-(4-Methylphenyl)ethyl]-N⁴-[(1S)-1-(4-nitrophenyl)ethyl]-1,3,5-triazine-2,4,6-triamine, N²-[2-(4-Hydroxy-3-methoxyphenyl)ethyl]-N⁴-[(1S)-1-(4-nitrophenyl)ethyl]-1,3,5-triazine-2,4,6-triamine, and N²-(2-Chlorophenylmethyl)-N⁴-(2-phenylethyl)-1,3,5-triazine-2,4,6-triamine.

7. A compound of Formula (I)

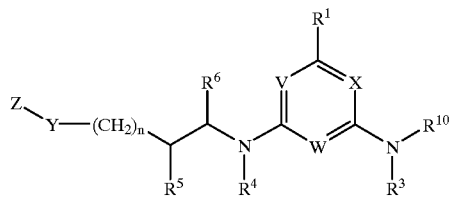

(I)

or pharmaceutically acceptable salt or hydrate thereof, wherein

V, W and X are each N;

Y is O, S(O)$_m$, CH$_2$, NR$^9$ or a covalent bond;

Z is selected from the group consisting of benzodioxolyl, cyclohexenyl, furanyl, indolyl, napthalenyl, thienyl and pyridinyl;
  optionally substituted with one to five groups, the same or different independently selected from the group consisting of halogen, C$_{1-4}$alkyl, C$_{1-4}$haloalkyl, O—C$_{1-4}$alkyl, cyano, hydroxy, nitro, NHSO$_2$C$_{1-6}$alkyl, NR$^7$R$^8$, C(O)NH$_2$ and C$_{1-3}$alkylene; and m and n are each independently 0, 1 or 2;

R$^1$ is halogen or NR$^7$R$^8$;

R$^2$ is C$_{1-4}$alkyl substituted with Z', wherein
  Z' is selected from the group consisting of benzodioxolyl, cyclohexenyl, furanyl, indolyl, napthalenyl, thienyl and pyridinyl;
    optionally substituted with one to five groups, the same or different independently selected from the group consisting of halogen, C$_{1-4}$alkyl, C$_{1-4}$haloalkyl, O—C$_{1-4}$alkyl, cyano, hydroxy, nitro, NHSO$_2$C$_{1-6}$alkyl, NR$^7$R$^8$ and C(O)NH$_2$ R$^3$ is hydrogen, C$_{1-6}$alkyl or C$_{3-7}$cycloalkyl;

R$^4$ and R$^5$ are independently hydrogen or C$_{1-6}$alkyl or together are C$_{2-3}$alkylene;

R$^6$ is hydrogen or C$_{1-3}$alk(en)ylene
  provided that if R$^6$ is C$_{1-3}$alk(en)ylene, it is attached to Z;

R$^7$ and R$^8$ are independently selected from the group consisting of hydrogen, C$_{1-6}$alkyl, C$_{3-7}$cycloalkyl, SO$_2$C$_{1-6}$alkyl;
  or R$^7$ and R$^8$ together with the nitrogen to which they are attached form a 5 to 8 membered heterocycle;
    said heterocycle optionally containing a second heteroatom selected from the group consisting of N, O and S;
    said heterocycle being optionally substituted with up to three of the same or different substituents independently selected from C$_{1-6}$alkyl or O—C$_{1-6}$alkyl; and R$^9$ is hydrogen or (C$_{1-6}$)alkyl.

8. A compound according to claim 7 wherein

Z' is selected from the group consisting of benzodioxolyl, cyclohexenyl, furanyl, indolyl, napthalenyl, thienyl and pyridinyl;
  optionally substituted with one to five groups, the same or different independently selected from the group consisting of halogen, C$_{1-4}$alkyl, C$_{1-4}$haloalkyl, O—C$_{1-4}$alkyl, cyano, hydroxy, nitro, NH SO$_2$ C$_{1-6}$alkyl, NR$^7$R$^8$ and C(O)NH$_2$.

9. A compound according to claim 7 wherein

Z is selected from the group consisting of benzodioxolyl, cyclohexenyl, furanyl, indolyl, napthalenyl, thienyl and pyridinyl;

optionally substituted with one to five groups, the same or different independently selected from the group consisting of halogen, $C_{1-4}$alkyl, $C_{1-4}$haloalkyl, O—$C_{1-4}$alkyl, cyano, hydroxy, nitro, NH SO$_2$ $C_{1-6}$alkyl, NR$^7$R$^8$, C(O)NH$_2$ and $C_{1-3}$alkylene.

10. A compound of formula (Ia)

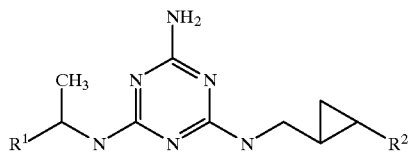

(Ia)

or pharmaceutically acceptable salt or solvate thereof, wherein

R' is phenyl optionally substituted with one or more of the same or different halogens; and R$^2$ is phenyl or pyridyl optionally substituted with one or more of the same or different halogens.

11. A compound according to claim 10 wherein

R$^1$ is phenyl optionally substituted with one or more of the same halogens; and R$^2$ is phenyl or pyridyl optionally substituted with one or more of the same halogens.

12. A compound according to claim 10 wherein

R$^1$ is phenyl optionally substituted with one halogen; and

R$^2$ is phenyl or pyridyl optionally substituted with one halogen.

13. A compound according to claim 10 wherein

R$^1$ is phenyl optionally substituted with fluoro; and

R$^2$ is phenyl or pyridyl optionally substituted with fluoro.

14. A compound according to claim 10 wherein

R$^1$ is unsubstituted phenyl; and

R$^2$ is monofluoro-phenyl or unsubstituted pyridyl.

15. A method of treating sleeping disorders, depression, hypertension, schizophrenia, anxiety, obsessive compulsive disorders and migraine comprising administration to a subject in need thereof an effective amount of a compound according to claim 10.

16. A method of inhibiting methyltransferase proteins comprising administration of an effective amount of a compound according to claim 10.

17. A compound according to claim 10 selected from the group consisting of (S,S)-trans-N-[2-(4-Fluoro-phenyl)-cyclopropylmethyly]-N'-(1-phenyl-ethyl)-[1,3,5]triazine-2,4,6-triamine,(S,S)-trans-N-[2-(2-Fluoro-phenyl)-cyclopropylmethyl]-N'-(1-phenyl-ethyl)-[1,3,5]triazine-2,4,6-triamine,(±)-trans-N-(1-Phenyl-ethyl)-N'-(2-pyridin-4-yl-cyclopropylmethyl)-[1,3,5]triazine-2,4,6-triamine,(±)-trans-N-[2-(2-Fluoro-phenyl)-cyclopropylmethyl]-N'-(1-phenyl-ethyl)-[1,3,5]triazine-2,4,6-triamine,(S,S)-trans-N-[2-(4-Fluoro-phenyl)-cyclopropylmethyl]-N'-[1-(4-fluoro)phenyl-ethyl]-[1,3,5]triazine-2,4,6-triamine and (±)-trans-N-[2-(4-Fluoro-phenyl)-cyclopropylmethyl]-N'-(1-phenyl-ethyl)-[1,3,5]triazine-2,4,6-triamine.

18. A compound according to claim 10 wherein R$^2$ is unsubstituted 4-pyridyl.

* * * * *